(12) United States Patent
Castro

(10) Patent No.: US 8,148,057 B2
(45) Date of Patent: Apr. 3, 2012

(54) METHODS, IMMUNOASSAYS AND DEVICES FOR DETECTION OF ANTI-LIPOIDAL ANTIBODIES

(75) Inventor: Arnold R. Castro, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 379 days.

(21) Appl. No.: 12/433,626

(22) Filed: Apr. 30, 2009

(65) Prior Publication Data

US 2009/0263825 A1 Oct. 22, 2009

Related U.S. Application Data

(63) Continuation-in-part of application No. 11/993,213, filed as application No. PCT/US2006/024117 on Jun. 20, 2006.

(60) Provisional application No. 60/693,120, filed on Jun. 21, 2005.

(51) Int. Cl.
 *G01N 33/53* (2006.01)
(52) U.S. Cl. ............. 435/4; 436/514; 436/518; 435/7.1; 435/283.1; 424/151.1; 424/262.1
(58) Field of Classification Search .................. 436/514, 436/518; 435/7.1, 4, 283.1; 424/151.1, 262.1
See application file for complete search history.

(56) References Cited

U.S. PATENT DOCUMENTS

| | | | |
|---|---|---|---|
| 4,632,901 A | 12/1986 | Valkirs et al. | |
| 4,952,409 A | 8/1990 | Bando et al. | |
| 5,091,187 A * | 2/1992 | Haynes | 424/450 |
| 5,141,850 A * | 8/1992 | Cole et al. | 436/525 |
| 5,776,489 A | 7/1998 | Preston et al. | |
| 5,780,319 A | 7/1998 | Maxfield et al. | |
| 6,235,489 B1 | 5/2001 | Jackowski | |
| 7,691,581 B2 | 4/2010 | Kintrup et al. | |
| 2003/0049857 A1 | 3/2003 | Chan | |
| 2003/0143636 A1 | 7/2003 | Simonson et al. | |

(Continued)

FOREIGN PATENT DOCUMENTS

EP 0985931 A2 3/2000

(Continued)

OTHER PUBLICATIONS

Cardiolipin Polyclonal Antibody, Unconjugated, web content from (http://www.biocompare.com/productlistings/3194/antibodies-search.html?s=cardiolipin).

(Continued)

*Primary Examiner* — Bao Thuy L Nguyen
(74) *Attorney, Agent, or Firm* — Klarquist Sparkman, LLP

(57) ABSTRACT

Compositions, methods and devices for the detection of anti-lipoidal antibodies and the diagnosis of disease, for example, syphilis, are described. In particular, a method for immobilizing a lipoidal antigen, comprising cardiolipin, lecithin, and cholesterol, on a solid support (such as a nitrocellulose membrane) is described. The ability to immobilize a lipoidal antigen on a membrane satisfies a long-felt need for a membrane-based assay for the detection of anti-lipoidal antibodies. Also described are immunoassay devices for concurrently performing treponemal and non-treponemal tests for syphilis.

26 Claims, 11 Drawing Sheets

U.S. PATENT DOCUMENTS

2004/0241876 A1    12/2004    Fannes

FOREIGN PATENT DOCUMENTS

| EP | 1 248 112 A2 | 10/2002 |
| WO | WO 88/08534 A1 | 11/1988 |
| WO | WO 00/75666 A1 | 12/2000 |

OTHER PUBLICATIONS

Harvey et al., The use of microporous polymer membranes in immunoassays, *IVD Technology Magazine*, web content from http://www.devicelink.com/ivdt/archive/96/05/007.html, accessed on Oct. 31, 2008, pp. 1-4.

Hörkköet al., Antiphospholipid Antibodies Are Directed against Epitopes of Oxidized Phospholipids, *J. Clin. Invest.*, Aug. 1996, pp. 815-825, vol. 98, No. 3.

Manzi et al., Biosynthesis and Turnover of O-Acetyl and N-Acetyl Groups in the Gangliosides of Human Melanoma Cells, *The Journal of Biological Chemistry*, Aug. 1990, pp. 13091-13103, vol. 265, No. 22.

Pedersen et al., Enzyme-linked immunosorbent assay for detection of antibodies to the venereal disease research laboratory (VDRL) antigen in syphilis, *Journal of Clinical Microbiology*, Sep. 1987, pp. 1711-1716, vol. 25, No. 9.

Perine et al., Immunity to Syphilis, *Infection and Immunity*, Nov. 1973, pp. 787-790, vol. 8, No. 5.

Pettit et al., Unheated Serum Reagin Test as a Quantitative Test for Syphilis, *Journal of Clinical Microbiology*, Feb. 1982, pp. 238-242, vol. 15, No. 2.

Rapport, Structure and specificity of the lipid haptens of animal cells, *J. Lipid Research*, Jan. 1961, pp. 25-36, vol. 2, No. 1.

Van Eijk et al., Enzyme linked immunosorbent assays with *Treponema pallidum* or axial filament of *T phagedenic* biotype Reiter as antigen: evaluation as screening tests for syphilis, *Genitourinary Medicine*, Dec. 1986, pp. 367-372, vol. 62, No. 6.

VDRL Antigen Test Kit, Product insert from Plasmatec Laboratory Products LTD, Bridport, Dorset, UK DT6 5BU.

White and Fuller, Visuwell Reagin, a Non-Treponemal Enzyme-Linked Immunosorbent Assay for Serodiagnosis of Syphilis, *Journal of Clinical Microbiology*, Oct. 1989, pp. 2300-2304, vol. 27, No. 10.

Young et al., Novel recombinant-antigen enzyme immunoassay for serological diagnosis of syphilis, *Journal of Clinical Microbiology*, Apr. 1998, pp. 913-917, vol. 36, No. 4.

Zielenski and Borkhardt, Studies on the lysozyme independence of immune immobilization of *Treponema pallidum* and the frequency of lysozyme autoantibodies in syphilitic sera, *Journal of Medical Microbiology*, 1997, pp. 669-674, vol. 46.

\* cited by examiner

Control Spot

Non-treponemal Antigen Spot

Treponemal Antigen Spot

METHODS, IMMUNOASSAYS AND DEVICES FOR DETECTION OF ANTI-LIPOIDAL ANTIBODIES

CROSS REFERENCE TO RELATED REFERENCES

This is a continuation-in-part of U.S. application Ser. No. 11/993,213, filed on Jan. 11, 2008, which is a §371 U.S. National Stage of PCT/US2006/024117, filed on Jun. 20, 2006, which was published in English under PCT Article 21(2), which in turn claims the benefit of U.S. Provisional Application No. 60/693,120, filed on Jun. 21, 2005. Each of these is incorporated herein by reference in its entirety.

FIELD

This disclosure concerns methods of immobilizing a lipoidal antigen to a solid support and related immunoassays and immunoassay devices (such as, test strips, flow-through devices, or lateral flow devices), which assays and devices are useful, for example, for detection of anti-lipoidal antibodies and/or diagnosis of disease (such as, syphilis).

BACKGROUND

Syphilis is a sexually transmitted disease (STD) caused by the spirochete bacterium *Treponema pallidum*. Over 100,000 cases of adult syphilis are reported worldwide each year. In addition, the disease is transmitted congenitally and affects 3,000 or more infants annually. The course of syphilis infection spans many years and may lead to a variety of clinical presentations, which are characterized by four stages.

The primary stage of syphilis infection occurs 10-100 days after bacterial infection, and is characterized by the appearance of one or more chancres (red, bloodless, painless ulcers typically less than 1 cm in diameter). The chancres may appear on the genitalia or elsewhere on the body. A chancre lasts 3-6 weeks and heals without treatment, leaving a small scar. Infected persons are contagious during this stage.

The secondary stage of syphilis infection is characterized by rash-like skin lesions that can cover part or all of the body. The skin lesions are generally painless and appear 1-6 months after the onset of the initial chancre(s). The skin lesions can resemble warts, pustules, or ulcers. Left untreated, they heal in 2-12 weeks without scarring. Fever, sore throat, weakness, weight loss, swelling of the lymph nodes, and loss of the eyelashes and/or part of the eyebrows can also occur during this stage of infection. In addition, the symptoms may progress to meningovascular syphilis, which is characterized by inflammation of the covering of the brain and spinal cord and/or changes in the vasculature of the brain. Infected persons are also contagious in the secondary phase.

The next stage of this disease is latent syphilis or the hidden stage. During this stage, the infected person appears to have recovered and is asymptomatic. This stage lasts for life in approximately two-thirds of persons who are not treated for syphilis. During the first year of latency, relapses of secondary stage symptoms may occur. Except during a relapse, infected persons are not contagious during this latent stage; however, children born to latently infected mothers within four years of the appearance of the primary chancre may contract congenital syphilis.

Tertiary or late syphilis is the final stage of untreated infection. This stage may occur as early as one year after infection or anytime thereafter with 10 to 20 years being most common. Benign syphilis, characterized by lesions called gummas, can occur in the bone, skin, and internal organs. Death is rare, but severe disfigurement and pain can occur. Cardiovascular syphilis is characterized by aortic aneurysms as well as other cardiovascular problems and frequently results in death. Neurologic involvement may occur in the early stages of syphilis as well as manifest as late stage symptoms. In the late stage disease, neurosyphilis may be asymptomatic or the patient may have severe neurologic problems such as possible dementia, insanity, impairment of mobility, blindness, deafness, or even death.

The immune response in syphilis involves production of (i) treponemal antibodies, which are specific for *T. pallidum* antigens, and (ii) anti-lipoidal antibodies, which recognize lipoidal material released from damaged host cells, lipoprotein-like material and possibly cardiolipin released from the treponemes. The mainstay of syphilis screening and diagnosis is serological testing for either or both of these two types of antibodies.

Tests for anti-lipoidal antibodies (often called "non-treponemal tests") are typically based on an antigen composed of naturally occurring cardiolipin, cholesterol and lethicin. The widely used non-treponemal tests (e.g., Venereal Disease Research Laboratory (VDRL) test and Rapid Plasma Reagin (RPR) test) monitor, either microscopically (e.g., VDRL test) or macroscopically (e.g., RPR test), the formation of a flocculent comprised of antigen-antibody complexes. Non-treponemal tests have the advantage of being widely available, inexpensive and convenient to perform on large numbers of specimens. Moreover, because anti-lipoidal antibody titers decrease with successful treatment for syphilis, eventually disappearing in most patients, while treponemal antibodies titers remain high for years or even a lifetime, non-treponemal tests are considered the better choice for monitoring treatment or testing for reinfection.

Treponemal tests are based on antigens derived from *T. pallidum* and include the *T. pallidum* particle agglutination (TP-PA), the fluorescent treponemal antibody-absorbed test (FTA-ABS) and enzyme immunoassays. Treponemal tests are used primarily to verify reactivity in non-treponemal tests. The treponemal test may also be used to confirm a clinical impression of syphilis in which the non-treponemal test is nonreactive. Treponemal tests are technically more difficult, time consuming, and expensive to perform and cannot be used to monitor treatment because the test will remain reactive for years or a lifetime in approximately 85% of persons successfully treated for syphilis.

Each of the above-described antibody tests is performed using a serum sample that is obtained in a clinical setting and sent to a laboratory for analysis. Therefore, test results are typically not available for several days after the sample is collected. Because of the frequent difficulty of tracing patients with STDs, the development of a rapid, point-of-care test is needed to aid the clinician in making a judgment, preferably on the day of testing.

Immunoassay devices (such as test strips, flow-through devices, or lateral flow devices), which offer rapid, on-site results, are available to qualitatively test serum levels of treponemal antibodies (e.g., DiaSys Corporation; ACON Laboratories, Inc.; Biokit, S.A.; Genix Technology; Standard Diagnostics; Cortez Diagnostics, Inc.; and Phoenix Bio-Tech Corp). However, analogous tests for anti-lipoidal antibodies have been more difficult to develop at least in part because the hydrophobic antigens of the anti-lipoidal antibodies (e.g., VDRL, USR or RPR antigens, or cardiolipin) resist attachment to solid supports, which is one element of an immunoassay device.

According to some experts, syphilis detection would be further aided by a combination of a non-treponemal test and a treponemal test for screening and diagnostic purposes. This is an approach advocated by the World Health Organization, Treponemal Infections, Technical Report Series 674, Geneva: WHO, 1982. An easy-to-use, rapid, point-of-care test capable of concurrently detecting both non-treponemal and treponemal antibodies would help address this long-felt need.

SUMMARY

Efforts to develop non-solution immunoassays for non-treponemal testing (or combined non-treponemal and treponemal testing) have been frustrated by the difficulty of attaching antigens specifically recognized by anti-lipoidal antibodies (referred to as "lipoidal antigens"), such as cardiolipin, VDRL antigen, USR antigen and the like, to a solid substrate, such as a nitrocellulose strip. For instance, the very small size of the cardiolipin molecule has resulted in poor localization of this molecule on a solid substrate. Although the size of the cardiolipin molecule could be increased by conjugating cardiolipin to larger molecules (such as proteins), such conjugations have resulted in the loss of cardiolipin antigenicity. More generally, the high degree of hydrophobicity of lipoidal antigens makes it difficult to bind such antigens to many solid surfaces, such as nitrocellulose and other microporous membranes. Additionally, lipoidal antigens have been traditionally prepared in an alcohol solvent which is not generally considered compatible with the use of a nitrocellulose strip.

The present disclosure provides an approach for reliably attaching lipoidal antigens (which are made up of, at least, cardiolipin, phosphatidylcholine (also referred to as "lecithin"), and cholesterol) to a solid substrate (such as, a microporous membrane) while maintaining the antigenicity and specificity of the antigen for anti-lipoidal antibodies. Using methods described herein, it is now possible to attach a lipoidal antigen to a variety of solid supports. The ability to attach the lipoidal antigen in this manner allows it to be used, for instance, in immunoassay devices for rapid, on-site testing of non-treponemal antibodies. In certain embodiments, disclosed immunoassay devices also incorporate *T. pallidum* antigens that are recognized by treponemal antibodies, such that the device conveniently and concurrently detects both non-treponemal (i.e., anti-lipoidal) and treponemal (i.e., anti-*T. pallidum*) antibodies.

In one particular example, a lipoidal antigen including cardiolipin, lecithin and cholesterol is attached directly to a solid substrate (such as, a microporous membrane) without the use of an anchor component. The attached lipoidal antigen is specific for the detection of anti-lipoidal antibodies and can therefore be used in a non-treponemal immunoassay device. For direct attachment of the lipoidal antigen to the solid substrate, the lipoidal antigen is processed to form micelles, for instance using agitation, disruption, sonication, or other methods known to one of skill in the art. The micelles can be separated by size, for instance by filtration, differential centrifugation, or a combination of sonication and differential centrifugation. The size fractionated micelles containing the lipoidal antigen can be applied directly to a variety of solid substrates to form an immobilized lipoidal antigen micelle without the use of an anchor antibody or component. The size fractionated lipoidal antigen micelle enters and is retained in pores of the solid substrate and is thereby immobilized. Once attached to the solid substrate, the immobilized lipoidal antigen micelle can be used to detect non-treponemal antibodies such as anti-lipoidal antibodies.

The foregoing and other features and advantages will become more apparent from the following detailed description of several embodiments, which proceeds with reference to the accompanying drawings.

DETAILED DESCRIPTION

I. Introduction

Figure 1:
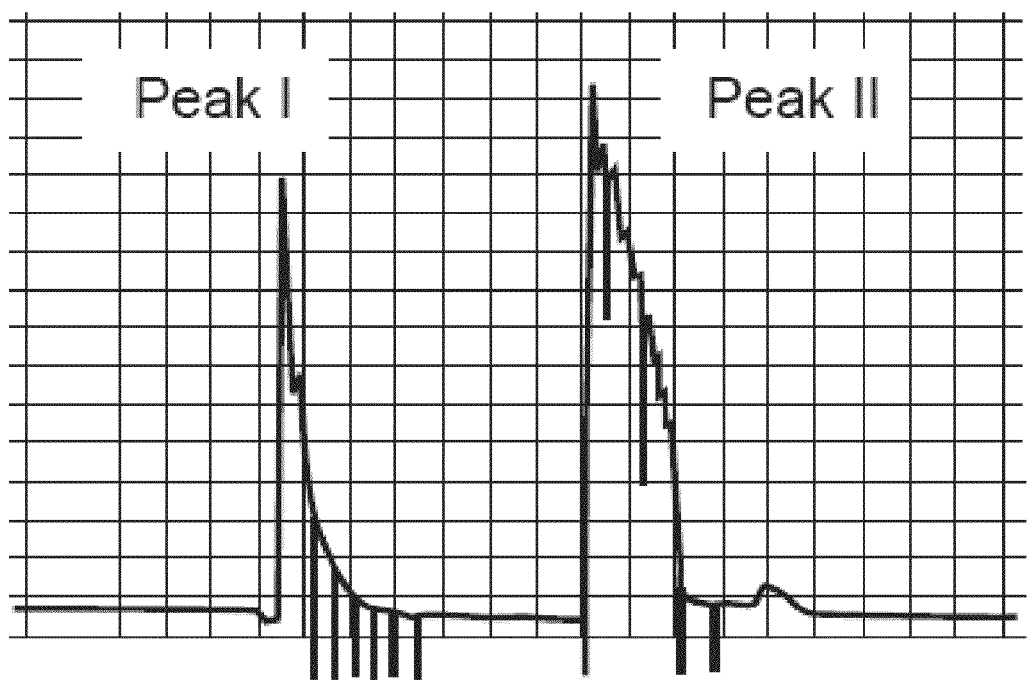
FIG. 1 is a tracing of the absorbance at 280 nm of the eluant from a Protein A column loaded with papain-digested purified IgG. An ISCO UA-5 Absorbance/Fluorescence Detector set to sensitivity 2 and chart speed 1.5 was used to collect the data. Glycine elution buffer was added to the column when the absorbance at 280 nm of the eluant returned to baseline after elution of Peak I.

Disclosed herein are immunoassay devices for determining the presence and/or amount of an anti-lipoidal antibody in a liquid sample, such as human sera. Such devices include a microporous substrate (such as nitrocellulose, nylon, polyvinylidene fluoride (PVDF), polyethersulfone, polycarbonate, polyester, cellulose acetate, mixed cellulose esters, or combinations thereof). The substrate includes, among other things, an anti-lipoidal capture area in which is immobilized a lipoidal antigen-anchor antibody complex. Such complex has an anchor antibody component, which is immobilized on the substrate, and a lipoidal antigen component, which is specifically bound by the anchor antibody and is thereby anchored to the substrate. The lipoidal antigen component includes cardiolipin, lecithin and cholesterol and can be specifically bound by anti-lipoidal antibodies (such as reagin antibodies present in *T. pallidum*-infected subjects).

In another embodiment, the substrate includes, among other things, an anti-lipoidal antibody capture area in which is immobilized a lipoidal antigen micelle. The lipoidal antigen micelle includes a lipoidal antigen that is applied to the substrate and is retained within pores of the substrate, thereby immobilizing the lipoidal antigen micelle to the substrate. The lipoidal antigen includes a USR antigen, a RPR antigen, a VDRL antigen, a synthetic VRDL antigen or cardiolipin, lecithin and cholesterol. The lipoidal antigen micelle can be specifically bound by anti-lipoidal antibodies (such as reagin antibodies present in *T. pallidum*-infected subjects).

Other device embodiments further include a sample application area and a flow path from the sample application area to the anti-lipoidal capture area. The sample application area is in liquid-continuous contact with the anti-lipoidal capture area such that a liquid sample placed in the sample application area can flow through or along the membrane (for example by capillary action or chromatographic flow) to the anti-lipoidal antibody capture area. The presence and/or amount of an anti-lipoidal antibody in the liquid sample can be detected by formation of an immunocomplex between the anti-lipoidal antibody and the immobilized lipoidal antigen-anchor antibody complex or the immobilized lipoidal antigen micelle. Some disclosed devices also include an absorbent pad, which is in contact with the membrane and serves as a reservoir for the sample after it contacts the capture area(s). In particular examples, a disclosed device is a lateral flow device or a flow-through device.

In some embodiments, the anchor antibody is a Fab fragment specific for cardiolipin. In other cases, a plurality of Fab fragments produced from immunoglobulins isolated from one or more *T. pallidum*-infected subjects serve as anchor antibodies. Some device embodiments include a lipoidal antigen that is a USR antigen, a VDRL antigen, or a synthetic VDRL antigen. In some cases (for example, for a flow-through device), a substrate (such as a nitrocellulose membrane) has an average diameter pore size from about 0.2 µm to about 8 µm. In other instances (for example, for a lateral-flow device), a substrate (such as a nitrocellulose membrane) has an average diameter pore size up to about 20 µm. In still other device embodiments, the anti-lipoidal antibody capture area comprises one or more lines, which, in some examples, can have a width from about 8 mm to about 15 mm.

In exemplary devices, the lipoidal antigen-anchor antibody complex is immobilized on the membrane by a method involving (a) contacting the lipoidal antigen with one or more anchor antibodies specific for at least one of cardiolipin, lecithin, or cholesterol to form the lipoidal antigen-anchor antibody complex; and (b) applying the lipoidal antigen-anchor antibody complex to the membrane. In more specific examples, the lipoidal antigen-anchor antibody complex is immobilized on the membrane by a method involving (i) immobilizing an anchor antibody specific for at least one of cardiolipin, lecithin, or cholesterol on the membrane; (ii) blocking non-specific binding sites on the membrane; (iii) contacting the immobilized anchor antibody with lipoidal antigen to form a lipoidal antigen-anchor antibody complex; and (iv) washing the membrane to remove any unbound lipoidal antigen.

Disclosed examples of the device provide an anchor antibody bound to an epitope naturally occurring in a component of the lipoidal antigen (e.g., cardiolipin or cholesterol) and not to a derivative group introduced into the antigen for the purposes of providing a binding site for the anchor antibody. For example, the anchor antibody does not bind to a biotinylated component of the lipoidal antigen (such as biotinylated lecithin or cardiolipin).

In some embodiments, a lipoidal antigen (such as a VDRL or USR antigen) is processed to form micelles, and the micelles are separated by size, for instance by sonication or differential centrifugation such that they can be applied directly to a microporous substrate. When small lipoidal antigen micelles, for instance, those having an average diameter of less than about 5 microns, for instance, less than about 3 microns, less than about 1 micron, less than about 0.9 microns, less than about 0.8 microns, less than about 0.7 microns, less than about 0.6 microns, less than about 0.5 microns, less than about 0.4 microns, less than about 0.3 microns, less than about 0.2 microns, or even smaller, the small lipoidal antigen micelles can be applied directly to a porous substrate (for example, a microporous membrane such as nitrocellulose) to form immobilized lipoidal antigen micelles without the use of an anchor antibody. In several embodiments, small lipoidal antigen micelles migrate from the area of application into pores of the microporous substrate such as the detection zone (or anti-lipoidal antibody capture area) and are retained and immobilized therein.

In a further embodiment, small lipoidal antigen micelles may also attach to non-pore areas of the microporous substrate as a result of electrostatic and charge interactions between negative charges of the lipoidal antigen and positive charges of the microporous substrate. However, the binding affinity and reproducibility of electrostatic interactions between the microporous membrane and the lipoidal antigen in the non-pore area of the microporous substrate is considered weak and/or non-specific when compared to the binding affinity of an immobilized lipoidal antigen micelle within a pore of the microporous substrate. The methods of immobilizing a lipoidal antigen micelle to a pore of a microporous substrate as disclosed herein can be used with any solid support to which the lipoidal antigen micelle will attach in a manner that substantially resists detachment when washed with an aqueous solution, such as when contacted with a liquid sample (such as a biological sample).

In exemplary devices, the lipoidal antigen micelle is immobilized on the microporous membrane by a method involving applying directly the lipoidal antigen micelle to the microporous membrane. In a non-limiting example, the lipoidal antigen is processed to a lipoidal antigen micelle by size fractionation, sonication or a combination thereof. In more specific examples, the lipoidal antigen micelle is immobilized in a pore of the microporous membrane by a method involving (i) applying the lipoidal antigen micelle to the membrane to form an immobilized lipoidal antigen micelle within a pore of the microporous membrane; and (ii) washing the membrane to remove any unbound lipoidal antigen micelle.

In some embodiments, a disclosed immunoassay device further includes a treponemal capture area having either (a) an immobilized treponemal antigen capable of being specifically bound by an anti-*T. pallidum* antibody, or (b) an immobilized anti-*T. pallidum* antibody that specifically binds a mobile treponemal antigen. In these embodiments, a liquid sample applied in the sample application area can flow through or along the membrane to the anti-lipoidal antibody capture area and to the treponemal capture area.

Also disclosed are lateral flow devices for determining the presence and/or amount of an anti-lipoidal antibody in a liquid sample. These devices typically include a sample application area and a separate anti-lipoidal antibody capture area such as a detection zone, in which an immobilized anchor antibody-lipoidal antigen complex or an immobilized lipoidal antigen micelle is provided. Any liquid (such as a liquid biological sample) applied in the sample application area flows along a path of flow from the sample application area to the anti-lipoidal antibody capture area. The path of flow may continue to a downstream absorbent pad associated with the lateral flow device, which acts, at least in part, as a liquid reservoir. Formation of an immunocomplex between the anti-lipoidal antibody and the immobilized lipoidal antigen complex or the immobilized lipoidal antigen micelle can be detected to determine the presence and/or amount of the anti-lipoidal antibody in the liquid sample. In several embodiments, the detection zone of the device includes pores of a predetermined size.

In some embodiments of the lateral flow device, a conjugate pad is placed in the path of flow from the sample application area to the anti-lipoidal antibody capture area. The conjugate pad includes a mobile or mobilizable detector reagent for an anti-lipoidal antibody, such that flow of liquid through the conjugate pad moves the detector reagent to the anti-lipoidal antibody capture area. Formation of an immunocomplex among the detector reagent, anti-lipoidal antibody, and the anchor antibody-lipoidal antigen complex provides a visible or otherwise detectable indicator of the presence of the anti-lipoidal antibody in a biological specimen. In another embodiment, formation of an immunocomplex among the detector reagent, anti-lipoidal antibody, and the immobilized lipoidal antigen micelle in the detection zone provides a visible or otherwise detectable indicator of the presence of the anti-lipoidal antibody in a biological specimen. In alternative embodiments, the detector reagent is not supplied in a conjugate pad, but is instead applied to the microporous membrane, for example from a developer bottle.

Examples of a detector reagent include a labeled Protein A, Protein G, or anti-human antibody, in which the label is one or more of an enzyme, colloidal gold particle, colored latex particle, protein-adsorbed silver particle, protein-adsorbed iron particle, protein-adsorbed copper particle, protein-adsorbed selenium particle, protein-adsorbed sulfur particle, protein-adsorbed tellurium particle, protein-adsorbed carbon particle, or protein-coupled dye sac.

Certain embodiments of the lateral flow device also include a treponemal capture area in the flow path from the sample application area. Such treponemal capture area may include, for example, an immobilized treponemal antigen having a binding affinity for a mobile anti-*T. pallidum* antibody or an immobilized anti-*T. pallidum* antibody having a binding affinity for a mobile *T. pallidum* organism or *T. pallidum* antigen. The lateral flow device may also have a mobile or mobilizable detector reagent specific for the treponemal antibody in the conjugate pad. The detector reagent for the treponemal antibody may be in the same or a different pad than the detector reagent for the anti-lipoidal antibody. In particular embodiments, a detector reagent specific for an anti-*T. pallidum* antibody comprises gold-conjugated Protein A, gold-conjugated Fc-specific Protein G, or gold-conjugated anti-human antibody (Fc portion). In other embodiments, a treponemal capture area can include an anti-treponemal antibody for capture of a mobile treponemal antigen present in a liquid sample. In such embodiments, a detector reagent for the mobile treponemal antigen can be a gold-labeled anti-treponemal antigen antibody.

The disclosed immunoassay devices (e.g., flow-through or lateral-flow device) can be used in methods for detecting anti-lipoidal antibodies and/or diagnosing syphilis in a subject by applying a biological sample (such as blood, serum, skin ulcer exudate, urine, saliva, or sputum) from a subject to a disclosed device and detecting formation of an immunocomplex among an anti-lipoidal antibody present in the sample, an anchor antibody-lipoidal antigen complex or an immobilized lipoidal antigen micelle, and an anti-lipoidal antibody detector reagent in the detection zone. Detection of formation of the immunocomplex in the capture area or detection zone indicates the presence of an anti-lipoidal antibody associated with *T. pallidum* infection and can be used to diagnose syphilis in the subject. In those embodiments in which the device includes a conjugate pad in the path of flow from the sample application area to the capture area, the detected complex includes the mobile or mobilizable detector. In other embodiments in which the detector reagent is applied to the device from an external source, the detected complex includes the externally applied detector. In some embodiments, a detector reagent is labeled Protein A, Fc-specific Protein G, or anti-human antibody.

In particularly advantageous embodiments of the method, the disclosed device is capable of detecting both the anti-lipoidal antibodies (which, for example, are an indicator of active infection) and anti-treponemal antibodies (which, for example, verify reactivity of the non-treponemal test). In those embodiments of the device which include the treponemal antigen, the method comprises detecting formation of a complex between an anti-*T. pallidum* antibody, an immobilized treponemal antigen, and a detector reagent in a capture area separate to, or in combination with, an anti-lipoidal antibody capture area. As with the detector reagent used for anti-lipoidal antibodies, the detector reagent for the treponemal antibodies can be provided on the device or applied from an external source.

Also disclosed herein are methods for immobilizing immunoreactive cardiolipin on a solid support (such as, nitrocellulose). Such methods involve (a) contacting a lipoidal antigen, including immunoreactive cardiolipin, with one or more antibodies specific for at least one component of the lipoidal antigen to form a lipoidal antigen-antibody complex; and (b) applying the lipoidal antigen-antibody complex to a solid support; wherein applying the lipoidal antigen-antibody complex to the solid support immobilizes the immunoreactive cardiolipin on the solid support. In particular examples, the lipoidal antigen is a USR antigen, a VDRL antigen, or a synthetic VDRL antigen. In other examples, the antibody is an antibody fragment that will not substantially react with Protein A, Fc-specific Protein G, or anti-human antibody (Fc portion) (such as, a Fab fragment). In still other examples, the antibody is isolated from serum of a *T. pallidum*-infected or *T. pallidum*-inoculated subject.

Other exemplary methods for immobilizing immunoreactive cardiolipin on a solid support, involve (a) immobilizing one or more antibodies specific for cardiolipin, lecithin and/or cholesterol on a solid support; (b) blocking non-specific binding sites on the solid support; (c) applying a lipoidal antigen, including immunoreactive cardiolipin, lecithin and/or cholesterol, to the solid support to form lipoidal antigen-immobilized antibody complexes; and (d) washing the solid support to remove any lipoidal antigen that is not specifically bound by the one or more immobilized antibodies.

Yet another exemplary method for immobilizing immunoreactive cardiolipin on a solid support, involves (a) applying a lipoidal antigen, including immunoreactive cardiolipin, lecithin and cholesterol in the form of a micelle, to the solid support to form an immobilized lipoidal antigen micelle in a pore of the solid support; and (b) washing the solid support to remove lipoidal antigen micelles that are not specifically bound to a pore of the solid support.

Also disclosed herein are kits for the diagnosis of syphilis. These kits include a disclosed device (such as a flow-through or lateral-flow device) and instructions for applying the biological sample to the sample application area or the device. The kit may also include instructions for interpreting results of the test.

The disclosed devices can be also used in methods for diagnosing lupus in a subject by analyzing a biological sample from the subject, by applying the biological sample to the device and detecting formation of a complex among the anti-lipoidal antibody, the anchor antibody-lipoidal antigen complex, and a detector reagent in the capture area. Detection of the formation of the complex in the capture area detects an anti-lipoidal antibody associated with lupus. In some instances, one or more co-factors (such as $\beta_2$-glycoprotein I) are present (such as, added to a sample) for the detection of lupus.

II. Abbreviations, Terms and Methods

Ab antibody
HPLC high pressure liquid chromatography
LFD Lateral flow device
PEG polyethylene glycol
PVA polyvinyl alcohol
PVDF polyvinylidene fluoride
PVP polyvinyl pyrrolidone
SDS sodium dodecyl sulfate
USR unheated serum regain Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Analyte: A target, such as an atom, molecule, group of molecules or compound of natural or synthetic origin (e.g., drug, hormone, enzyme, growth factor antigen, antibody, hapten, lectin, apoprotein, or cofactor) sought to be detected or measured that is capable of binding specifically to immobilized lipoidal antigens described herein. Analytes may include, but are not limited to biological analytes, antibodies, drugs, hormones, antigens, haptens, lectins, apoproteins, or cofactors. In some embodiments, the analyte includes antibodies, such as anti-lipoidal antibodies (e.g., anti-cardiolipin antibodies), produced in response to infection by *T. pallidum*. In other embodiments, the analyte includes anti-lipoidal antibodies produced in response to any of (i) an autoimmune disease, such as lupus, (ii) various venous and arterial thrombotic disorders, including cerebral infarction, (iii) deep venous thrombosis, (iv) thrombocytopenia Antibody: A protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies are naturally produced in plants and animals in response to antigens presented to the immune system. Naturally produced antibodies may be found, for example, in the serum of an animal. For example, a person infected with *T. pallidum* typically will produce antibodies at least against *T. pallidum* antigens and antibodies against lipoidal material that results from the treponemal infection (e.g., anti-lipoidal antibodies), for example, from host cells damaged by the infection.

Antibodies may exist as intact immunoglobulins or as a number of well-characterized fragments produced by digestion with various peptidases or by recombinant DNA methods. Exemplary antibody fragments include, for example, Fab, Fab', F(ab')$_2$, Fv, Fd, dAb, complementarity determining regions (CDR), and single-chain antibodies (scFv). A Fab fragment is a monovalent fragment consisting of the VL, VH, CL and CH1 domains; an F(ab')$_2$ fragment is a bivalent fragment comprising two Fab fragments linked by a disulfide bridge at the hinge region; an Fd fragment consists of the VH and CH1 domains; an Fv fragment consists of the VL and VH domains of a single arm of an antibody; and a dAb fragment consists of a VH domain (see, e.g., Ward et al., *Nature*, 341: 544-546, 1989; *Fundamental Immunology*, W. E. Paul, ed., Raven Press, N.Y., 1993).

While certain antibody fragments are defined in terms of the digestion of an intact antibody, it will be appreciated that Fab fragments or other antibody fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antigen: A chemical or biochemical compound, composition, structure, determinant, antigen or portion thereof that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

[Antigen-specific] Hyperimmune serum: Polyclonal antiserum having specificity for a particular antigen (such as, a lipoidal antigen and/or cardiolipin), which antiserum is produced in a subject in response to repeated challenge (e.g., by injection, infection or other route) with the antigen of interest (or an organism or other composition containing or producing the antigen of interest).

Anti-lipoidal antibody: An antibody (such as IgM or IgG) having specificity for a lipoidal antigen (see below). In some instances, anti-lipoidal antibodies are produced by the immune system of a subject (such as a human) in response to a disease state, such as a microbial (e.g., bacterial) infection. For example, this term contemplates anti-lipoidal antibodies produced as a consequence of *T. pallidum* infection. Although not bound by theory, it is thought that anti-lipoidal antibodies in subjects infected with *T. pallidum* are produced as the result of lipids released from host cells and/or lipoprotein-like material and possibly cardiolipin released from treponemes. Anti-lipoidal antibodies may also be produced in response to non-treponemal diseases, including, for example (i) an autoimmune disease, such as lupus (Harris et al., *Clin. Rheum. Dis.*, 11:591-609, 1985), (ii) various venous and arterial thrombotic disorders, including cerebral infarction (Harris et al., *Clin. Exp. Rheumatol.*, 2:47-51, 1984), (iii) deep venous thrombosis (Mueh et al., *Ann. Intern. Med.*, 92:156-159, 1980), (iv) thrombocytopenia (Harris et al., *Clin. Rheum. Dis.*, 11:591-609, 1985), (v) pulmonary embolism (Anderson and Ali, *Ann. Rheum. Dis.*, 43:760-763, 1984), or (vi) recurrent fetal loss with placental infarction (Derue et al., *J. Obstet. Gynaecol.*, 5:207-209, 1985). Anti-lipoidal antibodies found in non-treponemal diseases may specifically bind a lipoidal antigen in the presence of one or more co-factors (such as $\beta_2$-glycoprotein I).

Anti-lipoidal antibodies for use in some embodiments of the methods and compositions (e.g., devices) disclosed herein can be of any derivation, but often will be found in the serum of a subject.

Binding affinity: A term that refers to the strength of binding of one molecule to another at a site on the molecule. If a particular molecule will specifically bind to or specifically associate with another particular molecule, these two molecules are said to exhibit binding affinity for each other. Binding affinity is related to the association constant and dissociation constant for a pair of molecules, but it is not critical to the invention that these constants be measured or determined. Rather, affinities as used herein to describe interactions between molecules of the described methods and devices are generally apparent affinities (unless otherwise specified) observed in empirical studies, which can be used to compare the relative strength with which one molecule (e.g., an antibody or other specific binding partner) will bind two other molecules (e.g., an analyte and an analyte-label conjugate). The concepts of binding affinity, association constant, and dissociation constant are well known.

In general, the term "binding affinity" as used herein means the binding affinity of an antibody for an antigen. In one embodiment, affinity is calculated by a modification of the Scatchard method described by Frankel et al., *Mol. Immunol.*, 16:101-106, 1979. In several embodiments, a lipoidal antigen micelle is substantially immobilized within the pores of a microporous membrane i.e., has a specific binding affinity, when no more than about 1%, no more than about 2%, no more than about 5%, no more than about 10%, or no more than about 25% of the lipoidal antigen micelle becomes detached from the solid support when the support is contacted with a liquid sample for a time sufficient for the liquid sample to wet the solid support (e.g., for a time sufficient for a liquid sample to migrate along a membranous strip and contact an area where the lipoidal antigen micelle is immobilized). In contrast, a lipoidal antigen micelle that is not immobilized within a pore of the microporous membrane, such as a lipoidal antigen micelle that adheres to a non-pore area of the microporous membrane through electrostatic or charge interactions is considered to possess a weak and non-specific binding affinity.

Biological Sample: Any sample that may be obtained directly or indirectly from a subject, including whole blood, plasma, serum, tears, mucus, saliva, urine, pleural fluid, spinal fluid, gastric fluid, sweat, semen, vaginal secretion, sputum, fluid from ulcers and/or other surface eruptions (such as blisters, or abscesses), amniotic fluid, synovial fluid, cerebrospinal fluid, and/or extracts of tissues, cells or organs. The biological sample may also be a laboratory research sample such as a cell culture supernatant. The sample is collected or obtained using methods well known to those skilled in the art.

Capture area: A region of an immunoassay device (such as a flow-through device or lateral flow device) where a capture reagent (such as an anchor antibody-lipoidal antigen complex or a lipoidal antigen micelle) is immobilized. An immunoassay device may have more than one capture area, for example, a "primary capture area," a "secondary capture area," and so on. Often a different capture reagent will be immobilized in the primary, secondary, or other capture areas. Multiple capture areas may have any orientation with respect to each other on the substrate; for example, a primary capture area may be distal or proximal to a secondary (or other) capture area and visa versa. Alternatively, a primary capture area and a secondary (or other) capture area may be oriented perpendicularly to each other such that the two (or more) capture areas form a cross or a plus sign or other symbol.

Anti-lipoidal Antibody Capture Area: A capture area wherein an antigen capable of being specifically bound by an anti-lipoidal antibody (such as a lipoidal antigen-anchor antibody complex or a lipoidal antigen micelle) is immobilized as the capture reagent. As used herein an anti-lipoidal antibody capture area is interchangeable with a detection zone specific for the detection of an anti-lipoidal antibody.

Conjugate: When used in the verb form, the term "conjugate" means the coupling of one molecule (e.g., Protein A, Protein G, or anti-human IgG (Fc) antibody) to another molecule (e.g., colloidal gold). Such coupling may involve covalent or non-covalent (such as electrostatic or other) interactions between the components of the conjugate. Such coupling may be achieved by chemical means, either with or without the use of a linking group. When used in the noun form, the term "conjugate" means a coupled molecular complex formed by conjugation.

Detecting or Detection: Refers to qualitatively or quantitatively determining the presence of the analyte(s) under investigation (e.g., anti-lipoidal antibodies and/or anti-*T. pallidum* antibodies or treponemal antigens). "Detecting Formation of a Complex" refers to detecting a complex comprising a detector reagent by any method suitable for observing the particular label associated with the detector reagent; for instance, visual observation of a colored (or otherwise visible) label, measurement or visual detection of a fluorescent, chemiluminescent or radioactive label.

Detector Reagent (or Detection Agent): A reagent (or series of reagents) that permits the specific detection of a complex (or immunocomplex) between an analyte (such as an anti-lipoidal antibody) and a capture reagent (such as anchor antibody-lipoidal antigen complex or immobilized lipoidal antigen micelle). Further description of detector reagents and specific exemplary detector reagents are provided below.

Emulsion: A mixture of two immiscible fluids or liquids in which one phase is present as a colloidal dispersion in the other phase, which is referred to as the continuous, dispersing or solvent phase. Some emulsions will readily separate when they are allowed to stand undisturbed. Other emulsions may remain mixed for considerable lengths of time.

Epitope (or antigenic determinant): A site on the surface of an antigen molecule to which an antibody molecule binds; generally an antigen has several or many different antigenic determinants and reacts with antibodies of many different specificities. An "exogenous epitope" is an epitope that is not naturally found in an antigen molecule of interest and which is typically added to the antigen molecule to serve as a binding site for an antibody specific for (or other specific binding partner of) the exogenous epitope. An antigen molecule can be chemically or otherwise modified to include an exogenous epitope. For example, an antigen molecule can be biotinylated (i.e., derivatized with biotin) thereby producing an exogenous biotin epitope that can be specifically bound by an anti-biotin antibody or other biotin-specific binding partner (such as, avidin or strepavidin). In some instances, an exogenous epitope is an "epitope tag." Epitope tags include peptide sequences (typically less than about 15 amino acids, but can be even full-length protein sequences) to which an antibody can specifically bind. Commonly known epitope tags include hexa-His, octa-His, FLAG, HA, and numerous others.

Immunogenicity: The property of being able to evoke an immune response within an organism. For example, cardiolipin retains immunogenicity when an anti-lipoidal antibody has the ability to bind an epitope present in the cardiolipin.

Label: Any molecule or composition bound to an analyte, analyte analog, detector reagent, or binding partner that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulphur particles, protein-adsorbed tellurium particles, protein-adsorbed carbon particles, and protein-coupled dye sacs. The attachment of a compound (e.g., a detector reagent) to a label can be through covalent bonds, adsorption processes, hydrophobic and/or electrostatic bonds, as in chelates and the like, or combinations of these bonds and interactions and/or may involve a linking group.

Lipoidal Antigen: An antigen including (but not limited to) cardiolipin, lecithin and cholesterol that is capable of being specifically bound by anti-lipoidal antibodies. The nature of cardiolipin, lecithin and cholesterol as contemplated by the term "lipoidal antigen" is discussed in detail elsewhere in the specification.

Microporous membrane: A thin film or structure having microscopic-sized pores. A microporous membrane is similar in structure and function to a conventional filter. Typically, a microporous membrane has a rigid, highly voided structure with randomly distributed, interconnected pores. Although a microporous membrane with a defined distribution of interconnected pores is also contemplated by the instant invention. In both instances, these pores differ from those in a conventional filter by being extremely small, on the order of about 0.01 micron to about 20 microns in diameter. The microporous membranes may be isotropic or anisotropic. Isotropic microporous membranes possess a morphology in which the pore size within the membrane is substantially uniform throughout the membrane. Anisotropic (asymmetric) microporous membranes possess a morphology in which a pore size gradient exists across the membrane; that is, the membrane morphology varies from highly porous, larger pores at one membrane surface to less porous, smaller pores at the other membrane surface.

Generally, particles or molecules larger than the largest pores are generally rejected by the microporous membrane. Particles or molecules smaller than the largest pore but larger than the smallest pore are partially rejected, according to the pore size distribution of the membrane. Particles or molecules much smaller than the smallest pores pass through the membrane and are not retained or immobilized. Thus, separation of molecules or particles by microporous membranes is mainly a function of molecular size and pore size distribution. In general, only molecules or particles that differ considerably in size can be separated effectively by microporous membranes, for example, in ultrafiltration and microfiltration.

Microporous membranes at least permit liquids and soluble analytes to travel along or through the membrane, for example by capillary or chromatographic action. Microporous membranes are made of a wide variety of materials or composites of materials, including, for example, polyethylenes, polypropylenes, fluoropolymer, polyamides, polyethersulfone, nylon, polycarbonate, polyester, cellulose acetate, mixed cellulose esters, polyvinylidene fluoride, and/or nitrocellulose.

In several embodiments, the microporous membrane includes an anti-lipoidal antibody capture area or detection zone. In some embodiments, the microporous membrane contains two or more detection zones each with a different average pore size. For example, the anti-lipoidal antibody capture area may include a different average pore size compared to the remainder, or one or more other areas of the microporous membrane. In some embodiments, the microporous membrane and anti-lipoidal antibody capture area may be formed from a single piece of microporous material. By crushing or compressing a region of porous material, such as nitrocellulose, its pore size can be reduced such that an anchor antibody-lipoidal antigen complex cannot enter the compressed region, i.e., to form a filter zone. As an alternative, the pores of the microporous material can be partially blocked, to achieve the same effect.

As is well known in the art, the nominal pore size of a microporous membrane can be determined by hard particle challenge testing i.e., by determining the maximum diameter of spherical particles which can pass through the material. Alternatively, the pore size of a microporous material can be measured for example, by measuring its bubble point. The bubble point is the pressure required to force air through a wetted membrane, and correlates with the pore size as measured by particle retention. Any membrane known to those of ordinary skill in the art to be suitable for lateral-flow or flow-through devices is envisioned to be within the scope of the term "microporous membrane."

Protein A and Protein G: Protein A is a protein isolated from *Staphylococcus aureus*. Protein G is a protein isolated from a *Streptococcus* species. Both proteins have binding sites for the Fc portion of mammalian IgG. Native Protein G also contains binding sites for albumin, the Fab region of Igs, and membrane binding regions, which can lead to nonspecific binding; however, recombinant Protein G has been engineered to eliminate the albumin, Fab, and membrane binding sites while retaining the Fc binding site, which makes it specific for the Fc portion of IgG. As used herein "Protein G" refers to the Fc-specific recombinant form of Protein G (also referred to as "Fc-specific Protein G").

Specific binding partner (or binding partner): A molecule or composition capable of recognizing and binding to a specific structural aspect of another molecule or composition. Typical pairs of specific binding partners include antigen/antibody, hapten/antibody, hormone/receptor, nucleic acid strand/complementary nucleic acid strand, substrate/enzyme, inhibitor/enzyme, carbohydrate/lectin, biotin/(strept)avidin, and virus/cellular receptor.

The phrase "specifically binds to" refers to the ability of a first molecular species (such as an antibody) to preferentially bind to a second molecular species (such as an antigen recognized by the antibody) in comparison to other non-specific molecular species. Accordingly, the phrase "capable of being specifically bound by" refers to the ability of a first molecular species (such as an antigen) to be preferentially recognized and bound by a second molecular species (such as an antibody specific for the antigen) in comparison to other non-specific molecular species.

Subject: Living multi-cellular organisms, including vertebrate organisms, a category that includes both human and non-human mammals.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means "including A or B," or "including A and B." It is further to be understood that all molecular weight or molecular mass values are approximate and are provided solely for description. Suitable methods and materials used in the practice or testing of the disclosed subject matter are described below; however such materials and methods are illustrative only and not intended to be limiting. Methods and materials similar or equivalent to those described herein also can be used. All publications, patent applications, patents, and other references mentioned herein are incorporated by reference in their entirety to the extent permitted by applicable rules. In case of conflict, the present specification, including explanations of terms, will control.

III. Lipoidal Antigen

A lipoidal antigen is any antigen containing (without limitation) cardiolipin, lecithin and cholesterol, which antigen is capable of specifically binding an anti-lipoidal antibody. In some examples, a lipoidal antigen specifically binds an anti-lipoidal antibody (e.g., an anti-cardiolipin antibody) present in a *T. pallidum*-infected subject (such as, a human). Lipoidal antigens including cardiolipin (CL), lecithin (L) and cholesterol (Ch) have long been used in solution assays to detect anti-lipoidal antibodies in serum (see, e.g., prior discussion of "non-treponemal tests" for syphilis diagnosis). Specific exemplary CL/L/Ch-containing lipoidal antigens previously used in solution assays include the commonly known VDRL, RPR, and USR antigens (e.g., Venereal Disease Research Laboratory (VDRL) Slide Test, In: Larsen et al. (ed.), *A Manual of Tests for Syphilis,* 9th Edition, Washington D.C.: American Public Health Association, 1998, pp. 157-178; Pettit et al., "Unheated serum reagin [USR] test as a quantitative test for syphilis," *J. Clin. Microbiol.,* 15 (2): 238-242, 1982), and a synthetic form of the VDRL antigen ("Synthetic VDRL") described by Castro et al. (*Clin. Diagn. Lab. Immunol.,* 7 (4):658-661, 2000). Unfortunately, the lipoidal nature of such antigens has made it difficult to reliably attach any of these antigens to a solid support, such as a bibulous (e.g., microporous) membrane, like nitrocellulose or others. Accordingly, there has been a long-felt (but previously unmet) need to provide membrane-based assays (such as, flow-through or lateral flow immunoassay devices) for detection of anti-lipoidal antibodies, for instance, in biological samples. Such immunoassay devices would revolutionize, for example, point-of-care diagnosis of syphilis and other diseases characterized by the presence of anti-lipoidal antibodies. This disclosure describes, among other things, a method for immobilizing lipoidal antigens, such as the VDRL, USR, or Synthetic VDRL antigens, to membranous supports; thus, providing a means to satisfy a long-felt need in the art.

As discussed above, methods and compositions described herein contemplate a lipoidal antigen that includes (e.g., comprises or consists essentially of) cardiolipin, cholesterol and lecithin. These exemplary components of a lipoidal antigen are described in more detail below.

A. Cardiolipin

Cardiolipin is diphosphatidyl glycerol (specifically, 1,3-diphosphatidylglycerol), which has a backbone consisting of three molecules of glycerol joined by two phosphodiester bridges. The four hydroxyl groups of cardiolipin's external glycerol moieties are each esterified with a saturated or unsaturated fatty acid chain (typically from 14 to 18 carbons in length). As used herein, the term "cardiolipin" contemplates 1,3-diphosphatidylglycerol having any distribution of fatty acid side chains. Thus, the four fatty acid side chains of cardiolipin can independently vary in length (e.g., from about 14 to about 25 carbons, from about 14 to about 22 carbons, from about 14 to about 20 carbons, from about 14 to about 18 carbons, or from about 14 to about 16 carbons) and/or degree of saturation (e.g., from completely saturated to having about 6 double bonds, from completely saturated to having about 4 double bonds, or from completely saturated to having about 2 double bonds). Exemplary fatty acid side chains of cardiolipin, as contemplated herein, independently include myristoyl (14:0); palmitoyl (16:0); stearoyl (18:0); oleoyl (18:1); myristoleoyl (14:1); palmitoleoyl (16:1); petroselinoyl (18:1); linoleoyl (18:2); linolenoyl (18:3); eicosenoyl (20:1); arachidonoyl (20:4); erucoyl (22:1); DHA (22:6); or nervonoyl (24:1).

In some embodiments, cardiolipin is a naturally occurring form of cardiolipin. The fatty acid composition of naturally occurring cardiolipin is generally distributed according to a wide variety of natural occurring fatty acids such as palmitoyl (16:0); stearoyl (18:0); oleoyl (18:1); and linoleoyl (18:2). The most abundant fatty acid molecular species in naturally occurring forms of cardiolipin are linoleic acid at 90%, followed by oleic acid at 5%, and palmitric acid at 1%. In other embodiments, cardiolipin is a non-naturally occurring form (also referred to as "synthetic cardiolipin"). Non-limiting examples of synthetic cardiolipin include, for example, tetramyristoyl cardiolipin, tetraoleoyl cardiolipin, tetramyristoyl-bis-(L-α-glyceryl) phosphoric acid, bis(dipalmitoyl D,L-α-glycerylphosphoryl)-1,3 glycerol benzyl ether disodium salt, bis(dipalmitoyl D,L-α-glycerylphosphoryl)-1,5 pentanediol disodium salt, bis(dipalmitoyl D,L-α-glycerylphosphoryl)-1,3 propanediol disodium sal, bis (dipalmitoyl D,L-α-glycerylphosphoryl)-1,4 butanediol disodium salt, bis (dipalmitoyl D,L-α-glycerylphosphoryl)-1,2 ethanediol disodium salt, bis(dipalmitoyl D,L-α-glycerylphosphoryl)-methanediol disodium salt, bis(dipalmitoyl D,L-α-glycerylphosphoryl)-1,3 glycerol disodium salt, bis(benzylphosphoryl)-1,3-propanediol disodium salt, or D,L-α-dipalmitoyl bis-phosphatidic acid.

"Immunoreactive cardiolipin" is any form of cardiolipin (e.g., naturally occurring or synthetic cardiolipin) that specifically reacts with anti-lipoidal antibodies, such as anti-lipoidal antibodies present in a subject having syphilis or infected with *T. pallidum*.

B. Lethicin

Lecithin is the common name for phosphatidylcholine. Phosphatidylcholine is a glycerophospholipid, which is usually the most abundant phospholipid in animal and plants. It is a key building block of membrane bilayers, and is also the principal phospholipid circulating in the plasma. Phosphatidylcholine contains two fatty acid side chains. As used herein, the term "lecithin" contemplates phosphatidylcholine having any distribution of fatty acid side chains. Thus, the two fatty acid side chains of cardiolipin can independently vary in length (e.g., from about 14 to about 25 carbons, from about 14 to about 22 carbons, from about 14 to about 20 carbons, from about 14 to about 18 carbons, or from about 14 to about 16 carbons) and/or degree of saturation (e.g., from completely saturated to having about 6 double bonds, from completely saturated to having about 4 double bonds, or from completely saturated to having about 2 double bonds). Exemplary fatty acid side chains of lecithin, as contemplated herein, independently include myristoyl (14:0); palmitoyl (16:0); stearoyl (18:0); oleoyl (18:1); myristoleoyl (14:1); palmitoleoyl (16:1); petroselinoyl (18:1); linoleoyl (18:2); linolenoyl (18:3); eicosenoyl (20:1); arachidonoyl (20:4); erucoyl (22:1); DHA (22:6); or nervonoyl (24:1).

In some embodiments, lecithin is a naturally occurring form of lecithin. The fatty acid composition of naturally occurring lecithin includes palmitoyl (16:0), palmitoleoyl (16:1), linoleoyl (18:2), stearoyl (18:0), arachidonoyl (20:4), myristoyl (14:0), oleoyl (18:1), and linolenoyl (18:3). The relative percentages of fatty acids in naturally occurring lecithin vary depending upon the source of the lecithin (e.g., Balint et al., *J. Lipid Res.*, 6 (1):96, 1965). For example, lecithin in human gallbladder bile is reported to be about 45% 16:0, 4% 16:1, 4% 18:0, 16% 18:1, 23% 18:2, 4% 20:4 with traces of 18:3 and 14:0; and lecithin in human plasma is reported to be about 35% 16:0, 1% 16:1, 14% 18:0, 17% 18:1, 17% 18:2, 14% 20:4 with traces of 18:3 and 14:0. In other embodiments, lecithin is a non-naturally occurring form (also referred to as "synthetic lecithin").

Non-limiting examples of lecithin include, for example:

| Carbon Number | 1-Acyl | 2-Acyl |
|---|---|---|
| 14:0-14:0 | Myristoyl | Myristoyl |
| 14:0-16:0 | Myristoyl | Palmitoyl |
| 14:0-18:0 | Myristoyl | Stearoyl |
| 16:0-14:0 | Palmitoyl | Myristoyl |
| 16:0-16:0 | Palmitoyl | Palmitoyl |
| 16:0-18:0 | Palmitoyl | Stearoyl |
| 16:0-18:1 | Palmitoyl | Oleoyl |
| 16:0-18:2 | Palmitoyl | Linoleoyl |
| 16:0-20:4 | Palmitoyl | Arachidonoyl |
| 16:0-22:6 | Palmitoyl | Docosahexaenoyl |
| 18:0-14:0 | Stearoyl | Myristoyl |

-continued

| Carbon Number | 1-Acyl | 2-Acyl |
|---|---|---|
| 18:0-16:0 | Stearoyl | Palmitoyl |
| 18:0-18:0 | Stearoyl | Stearoyl |
| 18:0-18:1 | Stearoyl | Oleoyl |
| 18:0-18:2 | Stearoyl | Linoleoyl |
| 18:0-20:4 | Stearoyl | Arachidonoyl |
| 18:0-22:6 | Stearoyl | Docosahexaenoyl |
| 18:1-14:0 | Oleoyl | Myristoyl |
| 18:1-16:0 | Oleoyl | Palmitoyl |
| 18:1-18:0 | Oleoyl | Stearoyl |
| 14:1-14:1 | Myristoleoyl | Myristoleoyl |
| 14:1-14:1 | Myristelaidoyl | Myristelaidoyl |
| 16:1-16:1 | Palmitoleoyl | Palmitoleoyl |
| 16:1-16:1 | Palmitelaidoyl | Palmitelaidoyl |
| 18:1-18:1 | Petroselinoyl | Petroselinoyl |
| 18:1-18:1 | Oleoyl | Oleoyl |
| 18:1-18:1 | Elaidoyl | Elaidoyl |
| 18:2-18:2 | Linoleoyl | Linoleoyl |
| 18:3-18:3 | Linolenoyl | Linolenoyl |
| 20:1-20:1 | Eicosenoyl | Eicosenoyl |
| 20:4-20:4 | Arachidonoyl | Arachidonoyl |
| 22:1-22:1 | Erucoyl | Erucoyl |
| 22:6-22:6 | DHA | DHA |
| 24:1-24:1 | Nervonoyl | Nervonoyl |

Other particular lecithin examples include, without limitation, DL-α-dimyristoyl lecithin, L-α-dimyristoyl cephalin, L-α-dipalmitoyl lecithin, dipalmitoyl L-α-glycerophosphoric acid monocholine salt, L-α-dimyristoyl lecithin, D-α-dimyristoyl lecithin, L-α-distearoyl lecithin, stearoyl glycol-lecithin, 1,2-dioleoyl-sn-glycero-3-phosphocholine (18:1), 1,2-dilinoleoyl-sn-glycero-3-phosphocholine (18:2), 1,2-dimyristoyl-sn-glycero-3-phosphocholine (14:0), 1,2-dipentadecanoyl-sn-glycero-3-phosphocholine (15:0), 1,2-diphytanoyl-sn-glycero-3-phosphocholine (16:0), 1,2-dipalmitoyl-sn-glycero-3-phosphocholine (16:0), and 1-palmitoyl-2-oleoyl-sn-glycero-3-phosphocholine.

C. Cholesterol

Cholesterol is a steroid having, in one embodiment, the following structure:

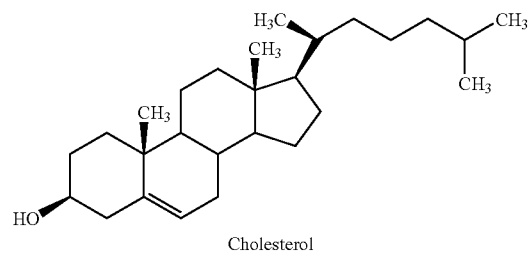

Cholesterol

Cholesterol is known to interact with phospholipids (such as, cardiolipin and lecithin) in membranes or membrane-like structures (such as liposomes or micelles). In these circumstances, the cholesterol molecule is believed to be oriented parallel to the fatty acid chains of the phospholipids, and the cholesterol hydroxyl group interacts with the phospholipid head groups.

In the formation of the lipoidal antigens disclosed herein, cholesterol is believed to stabilize the emulsion (e.g, micelle). Thus, for the purposes of this disclosure, the term "cholesterol" includes any form of cholesterol or other cholesterol derivative that is capable of stabilizing an emulsion which contains a lipoidal antigen. In some examples, stabilizing a lipoidal-antigen-containing emulsion refers to extending the time an emulsified lipoidal antigen remains in solution. For example, addition of cholesterol to a lipoidal antigen may extend the time such an antigen remains dispersed in a continuous phase of an emulsion (such as, in an ethanolic solution) by 5%, 10%, 15% or 25% as compared to a comparable antigen containing relatively less or no cholesterol.

Non-limiting examples of cholesterol derivatives include cholest-5-en-3 beta-yl-6-aminohexyl ether (AH-Chol; Zimmer et al., *Eur. J. Pharm. Biopharm.,* 47 (2): 175-8, 1999); poly(ethylene glycol) cholesteryl ethers (PEG(n)-Chols; Baba et al., *Traffic,* 2 (7):501-12, 2001; Ishiwata et al., *Biochim. Biophys. Acta,* 1359 (2):123-35, 1997); a cationic cholesterol derivative with a hydroxyethyl amino head group described by Nakanishi and Noguchi (*Adv. Drug Deliv. Rev.,* 52 (3):197-207, 2001); cholesterol hemisuccinate (Meuillet et al., *Eur. J. Pharmacol.,* 377 (2-3):241-52, 1999; dehydroergosterol (DHE), which differs from cholesterol in having three additional double bonds and an extra methyl group (Mukherjee, *Biophys. J.,* 75 (4):1915-1925, 1998); cationic derivatives of cholesterol which contain a tertiary amino head group with a different spacer arm (Takeuchi et al., *FEBS Lett.,* 397 (2-3):207-9, 1996); cholesteryl-3beta-carboxyamidoethylenedimethylamine (Noguchi et al., *FEBS Lett.,* 433 (1-2): 169-173, 1998); and N-[tris [(beta-D-galactopyranosyloxy) methyl]methyl]-N alpha-[4-(5-cholesten-3 beta-yloxy)succinyl]glycinamide (Kempen et al., *J. Medicin. Chem.,* 27:1306-1312, 1984). Further examples of cholesterol derivatives useful in the formation of membrane and membrane-like (e.g., liposomal or micellar) structures (like a disclosed lipoidal antigen) are described in U.S. Pat. Nos. 5,888,821; 5,043,164; 4,900,549; 4,442,037; 4,157,391; and 4,544,545, and European Pat. No. EP0606613.

D. Preparation of Lipoidal Antigen

In CL/L/Ch lipoidal antigen embodiments, cardiolipin, lecithin and cholesterol can be combined in any proportion that forms an antigen capable of being specifically bound by an anti-lipoidal antibody (such as, anti-cardiolipin antibody). In some instances, the lipoidal antigen will take the form of a micelle, liposome, membrane raft, or other membrane-like structure. In these structures, hydrophobic interactions cause the non-polar components (such as, the fatty acid chains) to aggregate and exclude water molecules from the "core." As one of ordinary skill in the art will appreciate, a micelle is a substantially spherical (or otherwise closed) non-bilayer structure having a hydrophobic interior composed of fatty acid chains (and not including an aqueous center). In comparison, a liposome is a substantially spherically arranged bilayer structure that is larger than a micelle and encloses an aqueous center. The type of structure formed by a CL/L/Ch mixture will depend, for example, on the length and degree of saturation of the fatty acid chains of cardiolipin and lecithin, on the temperature, on the ionic composition of the aqueous medium, and on the mode of dispersal of the phospholipids in the solution. In particular embodiments, a CL/L/Ch lipoidal antigen (such as, a VDRL, RPR, USR, or synthetic VDRL antigen) forms a micelle in an aqueous solution (such as an ethanolic solution). In more particular embodiments, a lipoidal antigen forms a micelle and does not form a liposome in an aqueous solution (such as an ethanolic solution).

A lipoidal antigen for use in a disclosed composition or method can be commercially obtained (e.g., Fisher (Cat. No. B40765), Fisher (Cat. No. 22-415-132), Fisher (Cat. No. 23-038010), True-Medix, IPX Overseas Corporation (Miami, Fla., USA), Cenogenics Corporation (Morganville, N.J., USA), Nova Century Scientific (Niagara Falls, N.Y., USA) as well as other suppliers) or produced by any method commonly known in the art. In one embodiment, a lipoidal antigen is produced as described in Example 1.

In some embodiments, a non-aqueous solution containing cardiolipin, lecithin and cholesterol (CL/L/Ch) is mixed with an aqueous solution to form an emulsion (e.g., micelle). Any non-aqueous solution in which cardiolipin, lecithin and cholesterol are each soluble (or partially soluble) can be used, including, for example, ethanol (such as absolute ethanol, 95% ethanol, or 70% ethanol), chloroform, hexane:ethanol (e.g., 9:1), toluene (e.g., 95%), dichloromethane, or benzene. In one example, a CL/L/Ch is prepared in absolute ethanol.

In some embodiments, a CL/L/Ch solution useful for preparing a lipoidal antigen can include from about 0.001% to about 0.1% cardiolipin (such as from about 0.005% to about 0.07%, from about 0.008% to about 0.05%, from about 0.01% to about 0.04%, or from about 0.025% to about 0.035%); from about 0.05% to about 0.5% lecithin (such as from about 0.07% to about 0.4%, from about 0.09% to about 0.3%, from about 0.1% to about 0.25%, or from about 0.14% to about 0.21%); and/or from about 0.2% to about 5% cholesterol (such as from about 0.4% to about 3%, from about 0.7% to about 2%, from about 0.8% to about 1%). In particular examples, a CL/L/Ch solution useful for preparing a lipoidal antigen includes about 0.03% cardiolipin (such as, naturally occurring cardiolipin), about 0.21% lecithin (such as, naturally occurring lecithin), and about 0.9% cholesterol. In another example, a CL/L/Ch solution useful for preparing a lipoidal antigen includes about 0.03% tetramyristoyl cardiolipin, about 0.14% 1-palmitoyl-2-oleoyl-sn-glycero-3-phosphocholine and about 0.9% cholesterol.

A CL/L/Ch solution useful for preparing a lipoidal antigen is mixed with an aqueous solution to form an emulsion of lipoidal antigen. The aqueous solution can include any solution in which a CL/L/Ch solution is immiscible, such as a saline solution (e.g., including 0.1-1.0 M NaCl, such as about 0.55 M NaCl). One exemplary aqueous solution includes 0.55 M NaCl, 0.05% (v/v) formaldehyde, 0.26 mM, 0.35 mM to 0.66 mM disodium hydrogen phosphate (for the dodecahydrate ($12\text{-}H_2O$), heptahydrate ($7\text{-}H_2O$), or anhydrous forms, respectively), and 1.2 mM potassium.

The ratio of CL/L/Ch solution to aqueous solution can be any ratio that will result in the formation of a lipoidal antigen emulsion (such as, CL/L/Ch-containing micelles). In some examples, the ratio of CL/L/Ch solution to aqueous solution ratio is about 1:10, about 1:15, about 2:33, or about 1:20. In other examples, the percentage of CL/L/Ch solution in an emulsion is about 3% (v/v), about 5% (v/v), about 8% (v/v), about 10% (v/v), or about 12% (v/v).

IV. Methods of Immobilizing Lipoidal Antigen

It is known that anti-lipoidal antibodies (e.g., reagin) in human serum will react with cardiolipin, lecithin and cholesterol-containing lipid antigens (such as, the RPR, VDRL, USR, or synthetic VDRL antigens). As discussed above, this knowledge formed the basis for solution-based, non-treponemal serological tests. Despite a long-felt need for membrane-based assays for syphilis testing, no one had previously recognized that a CL/L/Ch-containing lipoidal antigen could be immobilized on a membrane (or other solid support) using, as one example, the anti-lipoidal antibodies the antigen was specifically designed to detect. Unlike many other antigens, which have only one binding site for the antibody to be detected, the lipoidal antigen has many binding sites for anti-lipoidal antibodies. Thus, as disclosed herein, a non-saturating amount of anti-lipoidal antibody or other antibody that can specifically bind a lipoidal antigen (or, in particular examples, fragments of such antibodies, such as Fab fragments) can be used to anchor a lipoidal antigen to a solid support, such as a membranous surface (including, nitrocellulose, nylon and others) without adversely affecting the ability of the immobilized lipoidal antigen to further specifically bind anti-lipoidal antibodies present in a mobile phase (such as a biological sample).

A. Anchor Antibody

Antibodies useful to immobilize a lipoidal antigen to a solid support (such as a microporous membrane) in the disclosed compositions and methods include any antibody that is capable of specifically binding a lipoidal antigen, including, for example, anti-lipoidal antibodies from a *T. pallidum*-infected or *T. pallidum*-inoculated subject (such as, a human or a rabbit), anti-cholesterol antibodies, anti-cardiolipin antibodies, or anti-lecithin antibodies. As discussed in more detail below, antigen-binding fragments (such as, Fab fragments) of antibodies having the foregoing specificities can also serve as an anchor antibody in the disclosed compositions and methods. Anchor antibodies may be monoclonal or polyclonal. In specific embodiments, anchor antibodies are polyclonal (such as those antibodies isolated from hyperimmune serum from *T. pallidum*-infected humans or rabbits).

Polyclonal anti-lipoidal antibodies from *T. pallidum*-infected or *T. pallidum*-inoculated subjects can be obtained, for example, by isolating such antibodies from commercially available serum or by producing and isolating such polyclonal antibodies using methods commonly known in the art. Commercial suppliers of blood products (such as, serum) from *T. pallidum*-infected humans include New York Blood Center (New York, N.Y., USA); Biomedical Resources (Hatboro, Pa., USA); Life Diagnostics, a division of Life Therapeutics (formerly Serologicals) (Clarkston, Ga., USA); and Teragenix (formerly Millennium Biotech, Inc) (Ft. Lauderdale, Fla., USA). In other embodiments, polyclonal antisera containing anti-lipoidal antibodies can be produced by immunizing host animals (such as rabbits, mice, horses, goats and others) with *T. pallidum* and/or a lipoidal antigen (such as a VDRL antigen). Detailed procedures for monoclonal or polyclonal antibody production are described in Harlow and Lane (*Antibodies, A Laboratory Manual*, CSHL, New York, 1988). Specific non-limiting procedures for producing antibodies in a host animal using a CL/L/Ch-containing immunogen have been described by, e.g., Inoue and Nojima (*Biochim. Biophys. Acta*, 144 (2):409-414, 1967). Specific non-limiting protocols are available for producing anti-lipoidal antibodies by infection of a host animal with *T. pallidum* (see, e.g., Perine et al., *Infect. Immun.*, 8 (5):787-790, 1973). Moreover, custom antibody production services are commercially available (see, e.g., Spring Valley Laboratories (Woodbine, Md., USA); Maine Biotechnology Services (Portland, Me., USA); CovalAb UK (Cambridge, United Kingdom); 21st Century Biochemicals (Marlboro, Mass., USA) and numerous others). Such commercial services could be used to produce lipoidal-antigen-specific polyclonal or monoclonal antibodies.

In embodiments involving antiserum containing anti-lipoidal antibodies, an antibody fraction can be isolated from the serum using well known methods. Commercially available kits are suitable for use in isolating antibodies (including anti-lipoidal antibodies) from serum. Such kits are available from, for example, Millipore (Billerica, Mass., USA), Pierce (Rockford, Ill., USA); BioRad (Hercules, Calif., USA), and many others. One specific non-limiting method for isolating anti-lipoidal antibodies from serum is described in Examples 2-3.

Other exemplary anchor antibodies that can be used in the disclosed compositions and methods, include anti-cholesterol antibodies and anti-cardiolipin antibodies. Anti-cholesterol antibodies are present in human sera and can be isolated as described above for anti-lipoidal antibodies. Specific anti-cholesterol antibodies and/or protocols for producing and/or isolating anti-cholesterol antibodies can be found in Kruth et al. (*J. Lipid Res.*, 42:1492-1500, 2001), Alving et al. (*Biochem. Soc. Trans.*, 17:637-639, 1989), Swartz et al. (*Proc. Natl. Acad. Sci. USA*, 85:1902, 1988), Stollar et al. (*Mol. Immunol.*, 26 (1):73-79, 1989), and PCT Publication Nos. WO 00/06200, WO 97/21099, and WO 02/083100. Purified anti-cardiolipin antibodies are commercially available, for instance, from United States Biological (Swampscott, Mass., USA; e.g., Cat. No. C1375).

An anchor antibody for use in the present compositions and methods preferably (i) does not agglutinate with other antigen-bound anchor antibodies, and (ii) does not substantially bind to (or react with) a reagent (or series of reagents) used to detect an analyte of interest (such as, an anti-lipoidal antibody present in sample).

Agglutination is a process whereby multivalent antibodies form a cross-linked network bridged by their corresponding antigens, which must at least two binding sites for the antibody of interest (referred to as a "multivalent antigen"). Under these circumstances, a single antibody can bind to two different antigens and two different antibodies can bind to the same antigen. Agglutination occurs at certain concentrations of multivalent antibody with multivalent antigen. One exemplary way to avoid agglutination of an anchor antibody with lipoidal antigens (which are multivalent by nature), is to use Fab (or other monovalent) antibody fragments to anchor a lipoidal antigen. A monovalent antibody fragment cannot bind two antigens and, thereby, cannot serve to crosslink two different antigens. Methods of making monovalent antibody fragments are well known in the art. One non-limiting method for making and isolating Fab fragments is provided in Example 5.

An alternative, non-limiting method for avoiding agglutination is to apply anchor antibodies (regardless of valency) to a solid surface (such as, a membrane of a membrane-based immunoassay device) in the absence of lipoidal antigen; then, bind the lipoidal antigen to the immobilized antibody. In this alternative method, the antibodies and antigens are physically constrained from substantial crosslinking.

B. Solid Support

The methods of immobilizing a lipoidal antigen disclosed herein can be used with any solid support to which an anchor antibody will attach in a manner that substantially resists detachment when washed with an aqueous solution, such as when contacted with a liquid sample (such as a biological sample). Preferred solid support embodiments for disclosed immunoassay devices involve microporous membranes, such as nitrocellulose, nylon, polyvinylidene fluoride (PVDF), polyethersulfone, polycarbonate, polyester, cellulose acetate, mixed cellulose esters, or combinations thereof.

The surface of a solid support may be activated by chemical processes that cause covalent linkage of an agent (e.g., an anchor antibody, an anchor antibody-lipoidal antigen complex or a lipoidal antigen micelle) to the support. However, any other suitable method may be used for immobilizing an agent (e.g., an anchor antibody, an anchor antibody-lipoidal antigen complex or a lipoidal antigen micelle) to a solid support including, without limitation, ionic interactions, hydrophobic interactions, covalent interactions and the like. The particular forces that result in immobilization of an agent on a solid phase are not determinative for the methods and devices described herein.

A solid phase can be chosen for its intrinsic ability to attract and immobilize an agent, such as a capture reagent. Alternatively, the solid phase can possess a factor that has the ability to attract and immobilize an agent, such as an anchor antibody, an anchor antibody-lipoidal antigen complex or a lipoidal antigen micelle. The factor can include a charged substance that is oppositely charged with respect to, for example, an anchor antibody, an anchor antibody-lipoidal antigen complex or a lipoidal antigen micelle, or to a charged substance conjugated to the anchor antibody, the anchor antibody-lipoidal antigen complex or the lipoidal antigen micelle.

Numerous and varied solid supports are known to those in the art and include, without limitation, bibulous or microporous membranes (such as, nitrocellulose, nylon or PVDF), the walls of wells of a reaction tray, microtiter plate, test tubes, polystyrene beads, magnetic beads, and microparticles (such as latex particles). With regard to certain membrane embodiments, the porous structure of nitrocellulose has excellent absorption and adsorption qualities for a wide variety of reagents, for instance, anchor antibodies, anchor antibody-lipoidal antigen complexes or lipoidal antigen micelles. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

Except as otherwise physically constrained, a solid support may be used in any suitable shape, such as films, sheets, strips, or plates, or it may be coated onto or bonded or laminated to appropriate inert carriers, such as paper, glass, plastic films, or fabrics.

C. Immobilizing Anchor Antibody-Lipoidal Antigen Complexes

In some embodiments, lipoidal antigens are immobilized on a solid support by contacting in solution the lipoidal antigen with anchor antibodies specific for the lipoidal antigen (e.g., anti-lipoidal antibodies, anti-cholesterol antibodies, anti-lecithin antibodies, and/or anti-cardiolipin antibodies, and/or antigen-binding fragments of any of the foregoing) to form a lipoidal antigen-anchor antibody complex. In particular embodiments, lipoidal antigen is contacted in solution with a Fab fragment specific for the lipoidal antigen (e.g., a Fab fragment isolated from immunoglobulins in syphilitic human serum or serum from other *T. pallidum*-infected or -inoculated subject).

A lipoidal antigen-anchor antibody complex has a polypeptide component (i.e., an anchor antibody) and a lipid component (i.e., a lipoidal antigen). In contrast to lipids, it is well known in the art that polypeptides (e.g., proteins) will strongly adhere (via incompletely characterized interactions) to many types of solid supports and, in particular, to membranous supports (like nitrocellulose, nylon or PVDF) (see, e.g., Harvey, *Optimization of Nitrocellulose Membrane Based Immunoassays*, Keene, N.H.: Schleicher and Schuell, 1991; Wallis et al., *Ann. Rev. Microbiol.*, 33:413-437, 1979; Presswood, *Membrane Filtration: Applications and Problems*, New York, N.Y.: Marcel Dekker, 1981; Farrah et al., *Proc. Natl. Acad. Sci. USA*, 78:1229-1232, 1981; Batteiger et al., *J. Immunol. Meth.*, 55:297-307, 1982; Tijssen, *Practice and Theory of Immunoassays*, 8th ed, Amsterdam: The Netherlands Elsevier, 1993). Thus, via its association with a polypeptide component (e.g., anchor antibody) it is also now possible to strongly adhere (e.g., immobilize) a lipoidal antigen to a solid support (such as, nitrocellulose, nylon, or PVDF). Accordingly, the disclosed methods (and methods of making the disclosed compositions) contemplate contacting a solid support (such as a microporous membrane) with a solution of antigen-antibody complex wherein, through such contact, the antigen-antibody complex becomes substantially immobilized on the solid support. In some examples, an anchor antibody-lipoidal antigen complex is substantially immobilized on a solid support when no more than about 1%, no more than about 2%, no more than about 5%, no more than about 10%, or no more than about 25% of the antigen-antibody complex becomes detached from the solid support when the support is contacted with a liquid sample for a time sufficient for the liquid sample to wet the solid support (e.g., for a time sufficient for a liquid sample to migrate along a membranous strip and contact an area where a lipoidal antigen is immobilized).

To immobilize a lipoidal antigen to a solid surface, it is also contemplated that a solid surface (such as, nitrocellulose, nylon or PVDF) can be contacted with anchor antibody (e.g., in solution) in the absence of lipoidal antigen. The polypeptide anchor antibody strongly adheres to the solid surface, as discussed above, and is immobilized. Thereafter, the immobilized anchor antibody is contacted with lipoidal antigen (e.g., in solution). Specific binding of the lipoidal antigen by the immobilized anchor antibody serves to also immobilize the antigen. As discussed above, this antigen immobilization technique can be used to avoid agglutination in circumstances where the anchor antibody is multivalent and capable of mediating agglutination in the present of a multivalent antigen.

Under circumstances where it is desirable to detect a lipoidal-antigen-binding analyte (such as, anti-lipoidal antigens) using an immobilized lipoidal antigen, it is advantageous for the immobilized antigen to have exposed binding sites for the analyte. Accordingly, in the foregoing situations, amounts of anchor antibody that will not saturate (e.g., block) the majority (or predominantly all) of the analyte binding sites on a lipoidal antigen are used to form an anchor antibody-lipoidal antigen complex. A non-saturating amount of anchor antibody in an anchor antibody-lipoidal antigen complex is any amount of such antibody that will permit an analyte (e.g., anti-lipoidal antibodies in a mobile phase) to detectably bind the lipoidal antigen component of the complex. In some examples, no more than about 1%, no more than about 5%, no more than about 10%, no more than about 25%, no more than about 30% of the available anti-lipoidal antibody binding sites are blocked by the anchor antibody. In other examples, from 10 ng to about 1000 ng of anchor antibody in a 1 μl volume are reacted with an equal volume of lipoidal antigen prepared, for example, as described in Examples 1-3. In particular examples, from 25 ng to about 750 ng, from 50 ng to about 600 ng, from about 100 ng to about 500 ng, or from about 150 ng to about 400 ng anchor antibody are used to prepare an anchor antibody-lipoidal antigen complex.

Figure 9:
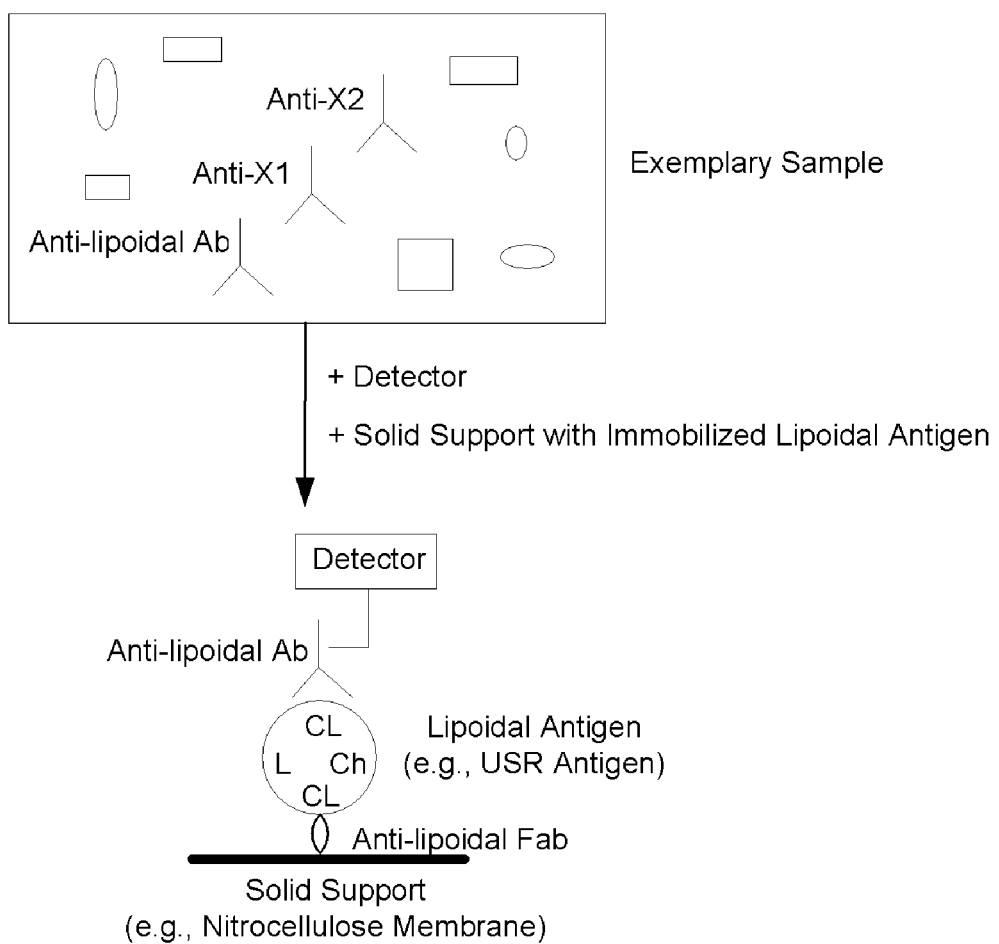
FIG. 9 is a schematic representation of one embodiment of an immobilized lipoidal antigen and the capture of an anti-lipoidal antibody analyte.

FIG. 9 illustrates one particular embodiment of a lipoidal antigen (e.g., a USR antigen) attached to a solid support (e.g., a nitrocellulose membrane) via an anchor antibody (e.g., an anti-lipoidal Fab). The figure further illustrates the capture by the immobilized lipoidal antigen of an anti-lipoidal antibody from an exemplary sample (such as, a serum sample) and a relationship between a detector, the captured anti-lipoidal antibody, the antigen, and the anchor antibody.

Particular examples exclude anchoring a lipoidal antigen to a substrate using an anchor antibody specific for a derivative group (such as, biotin, hexa-His, FLAG, or other epitope tag) which has been added to a lipoidal antigen component with the purpose of serving as an epitope for an anchor antibody. Such examples do not exclude including derivatized cardiolipin, derivatized lecithin and/or derivatized cholesterol as components of a lipoidal antigen; however, in such examples, the derivative groups of such derivatized components do not serve as epitopes for an anchor antibody.

1. Application of Anchor Antibody-Lipoidal Antigen Complex to Microporous Membranes Some disclosed methods and compositions contemplate an anchor antibody-lipoidal antigen complex (also referred to as a "capture reagent") to be attached to a microporous membrane (such as nitrocellulose, nylon or PVDF). The membrane serves to immobilize the capture reagent and to provide a surface across or through which an applied sample will flow or pass. Nitrocellulose (whether pure or modified in any manner known in the art) is a preferred membrane for the disclosed devices and methods. Nitrocellulose is thought to bind proteins by hydrogen bonding, hydrophobic interactions, and by electrostatic mechanisms (see, e.g., Millipore Corporation, *A Short Guide Developing Immunochromatographic Test Strips*, 2nd Edition, pp. 1-40, 1999, available by request at (800) 645-5476).

For protein-containing capture reagents, such as an anchor antibody-lipoidal antigen complex, the dipole of the nitrate ester of nitrocellulose is believed to interact with the strong dipole of the peptide bonds of the protein. Salts at high concentrations, detergents, and water in an application solution may weaken and destabilize electrostatic interactions between a nitrocellulose membrane and a protein to be applied to the membrane. Thus, it is preferable, although not required, to use a low molarity buffer, for example, 2-10 mM phosphate, borate or carbonate buffers, to solubilize protein-containing capture reagents for immobilization onto nitrocellulose.

The pH of an application solution may, but need not, be adjusted to increase binding of the capture reagent to a nitrocellulose membrane. For example, the solubility of a protein-containing capture reagent in an application solution is at a minimum when the pH of the application solution is within about +/−1 pH unit of the pI of the protein-containing capture reagent.

Optionally, 1 to 5% methanol, ethanol or isopropanol may be added to an application solution. An application solution may be applied to a membrane manually or in an automated manner. For example, a reagent dispensing module (e.g., Matrix 1600, Kinematic Automation, Twain Harte, Calif.) may be used to apply capture reagent to a microporous membrane (such as, nitrocellulose).

Typically, blocking of a microporous membrane in the disclosed methods and devices is not necessary. For example, proteins that are present in the sample and other blocking agents, which may be added, e.g., to a sample pad or conjugate pad of a lateral flow device, are generally sufficient to prevent an analyte from being non-specifically adsorbed onto the membrane. If optional blocking a membrane is desired for a particular application, useful blocking agents include, for example, gelatin (0.1%-0.5%), nonfat dry milk (0.5%-2%), casein (1%-2%), BSA (1%-2%), IgG (1%-2%), PVP 8-10 kD (0.5%-1.0%), and PVA 8-10 kD (0.5%-1.0%).

2. Other Methods for Attaching Lipoidal Antigen to Microporous Membranes

In other embodiments, the lipoidal antigen is attached directly to the microporous membrane (such as nitrocellulose, nylon or PVDF) without the use of an anchor antibody (also referred to as an "immobilized lipoidal antigen micelle or immobilized lipoidal antigen"). The membrane immobilizes the lipoidal antigen micelle and provides a surface across or through which an applied sample will flow or pass. Nitrocellulose (whether pure or modified in any manner known in the art) is a preferred membrane for the disclosed devices and methods. Nitrocellulose is thought to bind proteins by hydrogen bonding, hydrophobic interactions, and by electrostatic mechanisms (see, e.g., Millipore Corporation, *A Short Guide Developing Immunochromatographic Test Strips*, 2nd Edition, pp. 1-40, 1999, available by request at (800) 645-5476).

For direct attachment to the solid substrate, a solution suitable for the preparation of a lipoidal antigen is processed to form lipoidal antigen micelles, for instance using agitation, disruption, sonication, differential centrifugation or a combination thereof. The lipoidal antigen micelles are applied to the solid substrate, such as a microporous membrane. It will be readily apparent to one of ordinary skill in the art that other methods of micelle-formation can be applied to a lipoidal antigen solution to form lipoidal antigen micelles.

In some embodiments, a non-aqueous solution containing cardiolipin, lecithin and cholesterol (CL/L/Ch) is mixed with an aqueous solution to form a micelle. Any non-aqueous solution in which cardiolipin, lecithin and cholesterol are each soluble (or partially soluble) can be used, including, for example, ethanol (such as absolute ethanol, 95% ethanol, or 70% ethanol), chloroform, hexane:ethanol (e.g., 9:1), toluene (e.g., 95%), dichloromethane, or benzene.

In some embodiments, a CL/L/Ch non-aqueous solution useful for preparing a lipoidal antigen can include from about 0.001% to about 0.1% cardiolipin (such as from about 0.005% to about 0.07%, from about 0.008% to about 0.05%, from about 0.01% to about 0.04%, or from about 0.025% to about 0.035%); from about 0.05% to about 0.5% lecithin (such as from about 0.07% to about 0.4%, from about 0.09% to about 0.3%, from about 0.1% to about 0.25%, or from about 0.14% to about 0.21%); and/or from about 0.2% to about 5% cholesterol (such as from about 0.4% to about 3%, from about 0.7% to about 2%, from about 0.8% to about 1%). In particular examples, a CL/L/Ch solution useful for preparing a lipoidal antigen includes about 0.03% cardiolipin (such as, naturally occurring cardiolipin), about 0.21% lecithin (such as, naturally occurring lecithin), and about 0.9% cholesterol. In another example, a CL/L/Ch non-aqueous solution useful for preparing a lipoidal antigen includes about 0.03% tetramyristoyl cardiolipin, about 0.14% 1-palmitoyl-2-oleoyl-sn-glycero-3-phosphocholine and about 0.9% cholesterol.

A CL/L/Ch non-aqueous solution useful for preparing a lipoidal antigen is mixed with an aqueous solution to form a micelle. The aqueous solution used to form the micelle can include any solution in which a CL/L/Ch solution is immiscible, such as a saline solution (e.g., including 0.1-1.0 M NaCl, such as about 0.55 M NaCl). One exemplary aqueous solution includes 0.55 M NaCl, 0.05% (v/v) formaldehyde, 0.26 mM, 0.35 mM to 0.66 mM disodium hydrogen phosphate (for the dodecahydrate (12-$H_2O$), heptahydrate (7-$H_2O$), or anhydrous forms, respectively), and 1.2 mM potassium.

The ratio of CL/L/Ch non-aqueous solution to aqueous solution can be any ratio that will result in the formation of a lipoidal antigen emulsion (such as, CL/L/Ch-containing micelles). In some examples, the ratio of CL/L/Ch solution to aqueous solution ratio is about 1:10, about 1:15, about 2:33, or about 1:20. In other examples, the percentage of CL/L/Ch solution in an emulsion is about 3% (v/v), about 5% (v/v), about 8% (v/v), about 10% (v/v), or about 12% (v/v).

Once formed, the lipoidal antigen micelles can be separated for example, by average diameter size, for instance by filtration, differential centrifugation, or a combination of sonication and differential centrifugation. Additionally, other methods known to one of ordinary skill in the art that separate the lipoidal antigen micelle solution based on average diameter and/or molecular weight are contemplated herein.

In some embodiments, the lipoidal antigen micelles are centrifuged between about 6,000 rpm and about 10,000 rpm for about one hour at room temperature. The pellet, containing large micelles can be further centrifuged and/or sonicated until the large lipoidal antigen micelles are reduced to an appropriate size to enter and be retained within pores of a microporous membrane (i.e., immobilized). In another embodiment, a solution of lipoidal antigen micelles can be centrifuged between about 6,000 rpm and about 10,000 rpm for about one hour at room temperature, and the pellet resuspended in micelle resuspending solution, such as USR. The USR solution can be further centrifuged at about 13,000 rpm to about 16,000 rpm for about one hour at about 5° C. and the resulting pellet resuspended in micelle resuspension solution, thereby providing significantly smaller sized lipoidal antigen micelles as compared to the lipoidal antigen micelle starting solution.

In some embodiments, a lipoidal antigen micelle solution having undergone sonication and/or centrifugation is filtered using commercially available filters, such as Millipore™ or Qiagen™ filter columns, to produce a lipoidal antigen micelle solution containing appropriately sized micelles for use with a solid substrate, such as a microporous membrane. In some embodiments, a 5 micron, a 3 micron, a 1.8 micron, a 0.8 micron, a 0.65 micron, or even smaller filter membrane, or a combination thereof, is used to prepare a solution of lipoidal antigen micelles that can be applied directly to a microporous membrane. The use of one or multiple filters allows a user to determine and/or define the approximate average diameter of micelles in a lipoidal antigen solution and thus, determine which microporous membrane (based on average diameter pore size) is suitable to retain the lipoidal antigen micelles. In another example, a microporous membrane having an average diameter pore size of about 5 microns may require a user to filter a lipoidal antigen micelle solution through a filter of about 5 microns to produce micelles with an average diameter of about 5 microns that can enter, be retained and immobilized in the pores of the detection zone of the microporous membrane.

When small micelles, for instance, those having an average diameter of less than about 5 microns, for instance, less than about 3 microns, less than about 1 micron, less than about 0.9 microns, less than about 0.8 microns, less than about 0.7 microns, less than about 0.6 microns, less than about 0.5 microns, less than about 0.4 microns, less than about 0.3 microns, less than about 0.2 microns, or even smaller, the small micelles can be applied directly to the solid substrate to form an immobilized lipoidal antigen without the use of an anchor antibody.

In some embodiments, large lipoidal antigen micelles, for instance, lipoidal antigen micelles with an average diameter greater than about 5 microns, greater than about 10 microns, greater than about 12 microns, greater than about 15 microns, greater than 20 microns, or even larger, are subjected to further processing for example, by sonication, differential centrifugation and/or filtration, to produce lipoidal antigen micelles that possess a smaller average diameter, e.g., an average diameter within the small micelle range discussed above. Once sized appropriately, the further processed lipoidal antigen micelles can be applied directly to a solid substrate to form an immobilized lipoidal antigen without the use of an anchor antibody.

Non-limiting suitable average diameter pore sizes of a microporous membrane can be up to about 0.22 micron, from about 0.22 micron to about 0.45 micron, from about 0.22 micron to about 0.65 micron, from about 0.22 micro to about 0.8 micron, from about 0.22 micron to about 1.2 micron, from about 0.65 micron to about 3 microns, from about 0.65 micron to about 5 microns, from about 0.65 micron to about 8 microns, from about 5 microns to about 10 microns, or from about 5 microns to about 20 microns. In particular instances, average diameter pore sizes can be about 0.22 micron, about 0.45 micron, about 0.65 micron, about 0.8 micron, about 1 micron, about 1.2 micron, about 3 microns, about 5 microns, about 8 microns, about 10 microns, about 12 microns or about 20 microns. In one embodiment, the pore size of the microporous membrane has an average diameter from about 0.22 micron to about 20 microns.

In some embodiments, a microporous membrane may possess more than one pore size, for example when detecting one or more anti-lipoidal antibody/detector conformations. In one embodiment, at least 60%, at least 70%, at least 80%, at least 90%, or at least 95% of the pores in the microporous membrane comprise an average pore size of about 0.22 micron, about 0.45 micron, about 0.65 micron, about 0.8 micron, about 1.2 micron, about 3 microns, about 5 microns, about 8 microns, about 10 microns, about 12 microns, about 20 microns, or a combination thereof.

In some examples, a lipoidal antigen micelle is substantially immobilized on a solid support when no more than about 1%, no more than about 2%, no more than about 5%, no more than about 10%, or no more than about 25% of the lipoidal antigen micelle becomes detached from the solid support when the support is contacted with a liquid sample for a time sufficient for the liquid sample to wet the solid support (e.g., for a time sufficient for a liquid sample to migrate along a membranous strip and contact an area where the lipoidal antigen micelle is immobilized).

In one example, a method for making an immunoassay device for detection of anti-lipoidal antibodies includes providing a microporous membrane having a proximal sample application area and a detection zone with a predetermined pore size, applying a lipoidal antigen to the microporous membrane, where the lipoidal antigen is in micelle form, and the micelle is of a selected size to enter and be retained in the pores of the detection zone, thereby forming an immobilized lipoidal antigen in the detection zone of the immunoassay device. In some embodiments, the immunoassay device is a lateral flow or flow-through device and the lipoidal antigen micelles are applied in a linear distribution to form a test line. The method may also include washing the microporous membrane to remove unbound lipoidal antigen micelles from the microporous membrane.

In another example, a microporous membrane having a pore size with an average diameter of about 5 microns is used to immobilize lipoidal antigen micelles with an average diameter of about 5 microns. The lipoidal antigen micelles with an average diameter of about 5 microns are applied to the microporous membrane having a proximal sample application area and a detection zone with a predetermined pore size, the lipoidal antigen micelles migrate for example, by capillary action or chromatographic flow to the pores of the detection zone and are retained by the microporous membrane. The pores of the detection zone are of sufficiently small size to stop further migration of the lipoidal antigen micelles and instead retain and immobilize the micelles in the pores of the detection zone. It is contemplated herein that a lipoidal antigen micelle having a substantially similar average diameter with respect to the average diameter of a pore in a microporous membrane will be retained in the pore of the membrane. In another example, lipoidal antigen micelles having a significantly smaller average diameter (for example, less than about 1 micron) or larger average diameter (greater than about 10 microns) than a lipoidal antigen micelle with an average diameter of about 5 microns will not be retained by a microporous membrane with an average diameter pore size of about 5 microns and will therefore be washed away from the membrane prior to or during application of a sample.

In one embodiment, a method of making an immunoassay device for detection of anti-lipoidal antibodies contemplates (a) providing a microporous membrane having a proximal application area and a detection zone with a predetermined pore size, (b) applying a lipoidal antigen in micelle form to the microporous membrane, where the micelle enters and is retained in a pore of the detection zone of the microporous membrane, thereby forming an immobilized lipoidal antigen. In a further embodiment, the method optionally includes washing the microporous membrane to remove unbound or non-specifically bound lipoidal antigen micelles from the microporous membrane.

In one example, to immobilize a lipoidal antigen to a microporous membrane, it is contemplated herein that a lipoidal antigen micelle solution can be applied to the microporous membrane without filtering the micelle solution. After application of the lipoidal antigen micelle solution to the microporous membrane, the membrane can be washed or blocked by methods known in the art to remove any unbound or non-specifically bound lipoidal antigens, such as lipoidal antigen micelles not retained within pores of the microporous membrane. As discussed above, the lipoidal antigen micelles strongly adhere to and are retained in the pores of the microporous membrane and are thereby immobilized. Thereafter, the immobilized lipoidal antigen is contacted by anti-lipoidal antigens (e.g., anti-lipoidal antibodies in solution). Specific binding of the anti-lipoidal antigen by the immobilized lipoidal antigen serves to capture the anti-lipoidal antigen.

Typically, blocking of a microporous membrane in the disclosed methods and devices is not necessary. For example, proteins that are present in the sample and other blocking agents, which may be added, e.g., to a sample pad or conjugate pad of a lateral flow device, are generally sufficient to prevent an analyte from being non-specifically adsorbed onto the membrane. If optional blocking of a membrane is desired for a particular application, useful blocking agents include, for example, gelatin (0.1%-0.5%), nonfat dry milk (0.5%-2%), casein (1%-2%), BSA (1%-2%), IgG (1%-2%), PVP 8-10 kD (0.5%-1.0%), and PVA 8-10 kD (0.5%-1.0%).

The configuration of the pores on the microporous membrane is not considered essential, providing that the lipoidal antigen micelle is able to enter and be retained within the pores of the microporous membrane.

In one embodiment, the average diameter pore size of the membrane is substantially similar to the average diameter of the lipoidal antigen micelle. For example, where the lipoidal antigen micelle has an average diameter of about 0.8 microns the average diameter pore size of the microporous membrane is also about 0.8 microns. In another embodiment, where the lipoidal antigen micelle solution includes two different average diameters of lipoidal antigen micelles, for example about 0.8 microns and about 1.5 microns, it is preferred that the average diameter of the pores in the microporous membrane are about 0.8 microns and about 1.5 microns.

In some instances, the pores of the microporous membrane that retain the lipoidal antigen micelle in a lateral flow device are configured in a localized area (such as a line, square, rectangular or pre-defined anti-lipoidal antibody capture area). A positive reaction between immobilized lipoidal antigen micelles retained in the pores of the anti-lipoidal capture area upon exposure to non-treponemal antibodies present in a liquid sample applied to a lateral flow device can be observed as a variety of detectable signals, for example, as a change in color; a change in color intensity; or the appearance of color within the localized area. It will be readily apparent to one of ordinary skill in the art that other pore configurations of the microporous membrane are applicable and will be readily apparent from the disclosure provided herein. Additionally, it will also be apparent to the skilled artisan that additional means of detecting a positive reaction between an immobilized lipoidal antigen micelle retained in the pore of a microporous membrane and a non-treponemal antibody present in a sample are applicable, such as the use of a detector reagent.

A number of formats are suitable for the device of the present invention including lateral flow devices, test strips, dipsticks, slides, or cartridges. Many such formats are well known but the nature of the format is not critical providing that the essential features of the device can be provided. Any of the devices may include a region, cuvette or window for assessing a positive or negative (control) signal generated in operation of the device.

An immunoassay device made by the disclosed methods is contemplated by the present invention. The immunoassay device can be used to determine the presence or amount of an anti-lipoidal antibody in a liquid sample as the liquid sample flows along a flow path from the sample application area to the detection zone. The presence or amount of the anti-lipoidal antibody in the liquid sample can be detected for example, by formation of an immunocomplex between the anti-lipoidal antibody in the liquid sample and the immobilized lipoidal antigen micelle.

In another embodiment, the immunoassay can further include a treponemal capture area, for example, an immobilized treponemal antigen capable of being specifically bound by an anti-*T. pallidum* antibody, or an immobilized anti-*T. pallidum* antibody that specifically binds a mobile treponemal antigen.

To detect the formation of an immunocomplex between the anti-lipoidal antibody in a sample and the immobilized lipoidal antigen, the anti-lipoidal antibody capture area can include a single or multiple detection mechanisms and/or conformations. For example, the anti-lipoidal antibody area may have one or more lines or symbols that display positive conformation of an immunocomplex between the immobilized lipoidal antigen and the anti-lipoidal antibody, for example, as an appearance of color, change in color, change in color intensity within the anti-lipoidal capture area.

In one embodiment, the immunoassay device is a lateral flow device. The device may optionally further include a conjugate pad located in the flow path, where the conjugate pad includes a mobile or mobilizable detector reagent specific for the anti-lipoidal antibody. In this example, the detector reagent can be gold-conjugated Protein A, gold-conjugated Fc-specific Protein G, or gold-conjugated anti-human antibody (Fc portion).

In another embodiment, the conjugate pad may further comprise a mobile or mobilizable detector reagent specific for an anti-*T. pallidum* antibody or an mobile treponemal antigen. In this example, the detector reagent specific for the anti-*T. pallidum* antibody can be gold-conjugated Protein A, gold-conjugated Fc-specific Protein G, or gold-conjugated anti-human antibody (Fc portion), or the detector reagent for the mobile treponemal antigen can be gold-labeled anti-treponemal antigen antibody.

The disclosed immunoassay devices (e.g., flow-through or lateral-flow device) can be used in methods for detecting anti-lipoidal antibodies and/or diagnosing syphilis in a subject for example, by applying a biological sample (such as, blood, serum, skin ulcer exudate, urine, saliva, sputum or cerebrospinal fluid) from a subject to the disclosed device and detecting formation of an immunocomplex between the anti-lipoidal antibody, the immobilized lipoidal antigen micelle, and the anti-lipoidal antibody detector reagent in the detection zone. Detection of formation of the immunocomplex in the detection zone indicates the presence of the anti-lipoidal antibody associated with *T. pallidum* infection or the disease syphilis. In those embodiments in which the device includes a conjugate in the path of flow from the sample application area to the anti-lipoidal antibody capture area, the detected immunocomplex includes a mobile or mobilizable detector reagent. In other embodiments in which the detector reagent is applied to the device from an external source, the detected immunocomplex includes the externally applied detector reagent. In some embodiments, the detector reagent is labeled Protein A, Fc-specific Protein G, or anti-human antibody. It is contemplated herein that the detector reagent for use in an immunoassay device can be added to a biological sample prior to or concurrent with applying the biological sample to the immunoassay device.

In one embodiment, the disclosed device is capable of detecting both anti-lipoidal antibodies (which, for example, are an indicator of active infection) and anti-treponemal antibodies (which, for example, verify reactivity of the non-treponemal test). In those embodiments of the device which include a treponemal antigen, the method includes detecting the formation of a first immunocomplex between an anti-lipoidal antibody, an immobilized lipoidal antigen micelle and a detector reagent in the detection zone of the device and additionally, detecting the formation of a second immunocomplex between an anti-*T. pallidum* antibody, an immobilized treponemal antigen and a second detector reagent. In the above example, the formation of the second immunocomplex may occur in the detection zone of the device or in a separate capture area of the device. As with the detector reagent used for anti-lipoidal antibodies, the detector reagent for the treponemal antibodies can be provided on the device or applied from an external source.

Also disclosed herein are methods for immobilizing immunoreactive cardiolipin on a solid support (such as, nitrocellulose). Such methods involve (a) forming micelles from a lipoidal antigen solution, (b) separating the micelles by average diameter size, (c) collecting micelles having an average diameter of less than about 5 microns, and (d) applying the micelles having an average diameter of less than about 5 microns to the solid support. In particular examples, the lipoidal antigen is a USR antigen, a VDRL antigen, a synthetic VDRL antigen or cardiolipin, lecithin and cholesterol.

Microporous membranes of suitable pore sizes are made of a wide variety of materials or composites of materials, including, for example, polyethersulfone, nylon, polycarbonate, polyester, cellulose acetate, mixed cellulose esters, polyvinylidene fluoride, and/or nitrocellulose. Any microporous membrane known to those of ordinary skill in the art to be suitable for lateral-flow or flow-through devices is envisioned to be within the scope of the term "microporous membrane."

V. Immunoassay Devices

The discovery herein of a method to immobilize a lipoidal antigen (such as, a VDRL and/or USR antigen) to a solid support (such as, a microporous membrane, like nitrocellulose, nylon or PVDF) enables the production of immunoassay devices for the detection of lipoidal-antigen-binding analytes (such as, anti-lipoidal antibodies in biological samples from *T. pallidum*-infected subjects). In some examples, a disclosed immunoassay device permits detection of the presence (or absence) of anti-lipoidal antibodies in a biological sample for diagnosis of syphilis.

A. Representative Immunoassay Device Formats and Related Information

Immunoassay devices permit the performance of relatively inexpensive, disposable, membrane-based assays for the visual identification of the presence (or absence) of an analyte in a liquid sample. Such devices are usually formatted as freestanding dipsticks (e.g., test strips) or as devices having some sort of housing. Typically, an immunoassay device can be used with as little as about 200 µl of liquid sample, and detection of an analyte in the sample can (but need not) be complete within 2-5 minutes. In clinical assays, the sample may be urine, blood, serum, saliva, or other body fluids. In nonclinical tests, the sample may be a small volume of solution prepared from soil, dust, plants, or food, and similarly applied directly to the membrane test strip. In most instances, no ancillary instrumentation is required to perform such tests, and such devices easily can be used in clinics, laboratories, field locations, and the home even by inexperienced persons.

Immunoassay devices have been developed for the routine identification or monitoring of physiological and pathological conditions (e.g., infectious diseases, pregnancy, cancer, endocrine disorders) using different biological samples (e.g., urine, serum, plasma, blood, saliva), and for analysis of environmental samples (e.g., natural fluids and industrial plant effluents) for instance for contamination. Many of these tests are based on the highly specific interactions between specific binding pairs. Examples of such binding pairs include antigen/antibody, hapten/antibody, lectin/carbohydrate, apoprotein/cofactor and biotin/(strept)avidin. Furthermore, many of these tests involve devices (e.g., solid phase, lateral flow test strips, flow-through tests) with one or more of the members of a binding pair attached to a mobile or immobile solid phase material such as latex beads, glass fibers, glass beads, cellulose strips or nitrocellulose membranes (U.S. Pat. Nos. 4,703, 017; 4,743,560; 5,073,484).

One principle category of immunoassay is the "sandwich" assay. In general, sandwich immunoassay procedures call for mixing a sample, which may contain an analyte of interest (for example, anti-lipoidal antibody), with a detector reagent that specifically recognizes the analyte, for example, gold-conjugated Protein A, gold-conjugated Protein G, or gold-conjugated secondary antibody specific for anti-lipoidal antibody (e.g., anti-human Ab or anti-human Ab(Fc) secondary antibody). The detector reagent is mobile and typically is linked to a label or another signaling reagent, such as dyed latex, a colloidal metal sol, or a radioisotope. This mixture is then applied to a chromatographic medium (such as a microporous or bibulous membrane, like nitrocellulose, nylon or PVDF) containing a band or zone of immobilized antigens recognized by the analyte antibody of interest. The chromatographic medium often is in the form of a strip that resembles a dipstick or which can be incorporated into a housing, such as in a lateral flow device or flow-through device. When the complex of the molecule to be assayed and the detector reagent reaches the zone of the immobilized antigens on the chromatographic medium, binding occurs and the detector reagent complex is localized at the zone. This indicates the presence of the molecule to be assayed. This technique can be used to obtain quantitative or semi-quantitative results. Examples of sandwich immunoassays performed on test strips are described in, for example, U.S. Pat. Nos. 4,168,146 and 4,366,241.

In other common forms of membrane-based immunoassays, as typified by some home pregnancy and ovulation detection kits, a test strip (or dipstick) is "dipped" into a sample suspected of containing the subject analyte. Enzyme-labeled detector reagent is then added, either simultaneously or after an incubation period. The device next is washed and then inserted into a second solution containing a substrate for the enzyme. The enzyme label, if present, interacts with the substrate, causing the formation of colored products, which either deposit as a precipitate onto the solid phase or produce a visible color change in the substrate solution. EP-A 0 125 118 describes such a sandwich type dipstick immunoassay. EP-A 0 282 192 describes a dipstick device for use in competition type assays.

Flow-through type immunoassay devices were designed, in part, to obviate the need for incubation and washing steps associated with dipstick assays. Flow-through immunoassay devices involve a capture reagent (such as an anchor antibody-lipoidal antigen complex or a lipoidal antigen micelle) bound to a porous membrane or filter to which a liquid sample is added. As the liquid flows through the membrane, target analyte (such as, anti-lipoidal antibody) binds to the capture reagent. The addition of sample is followed by addition of detector reagent (such as, gold-conjugated Protein A or gold-conjugate anti-human IgG(Fc)). Alternatively, the detector reagent may be placed on the membrane in a manner that permits the detector to mix with the sample and thereby label the analyte. The visual detection of detector reagent provides an indication of the presence of target analyte in the sample. Representative flow-through immunoassay devices are described in U.S. Pat. Nos. 4,246,339; 4,277,560; 4,632,901; 4,812,293; 4,920,046; and 5,279,935; and U.S. Pat. Appl. Nos. 20030049857 and 20040241876.

Migration assay devices usually incorporate within them reagents that have been attached to colored labels, thereby permitting visible detection of the assay results without addition of further substances. See, for example, U.S. Pat. No. 4,770,853; PCT Publication No. WO 88/08534 and European Patent No. EP-A 0 299 428.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result.

U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; European Patent No. 0296724; WO 97/06439; and WO 98/36278.

There are also lateral flow type tests for the detection of small-analytes (MW 100-1,000 Daltons). Generally, these small analyte tests involve "typical" competitive inhibition to produce negative or indirect reporting results (i.e., reduction of signal with increasing analyte concentration), as exemplified by U.S. Pat. No. 4,703,017. However, several approaches have been developed for detecting small analytes using lateral flow tests that produce positive or direct reporting results (i.e., increase in signal with increasing analyte concentration). These include, for instance, U.S. Pat. Nos. 5,451,504; 5,451,507; 5,798,273; and 6,001,658.

U.S. Pat. No. 5,451,504 provides a method with three specific zones (mobilization, trap and detection) each containing a different latex conjugate to yield a positive signal. The mobilization zone contains labeled antibody to bind the analyte in the sample. In the trap zone, unbound, labeled antibody is then trapped by immobilized analyte analog. The detection zone captures the labeled analyte-antibody complex.

U.S. Pat. No. 5,451,507 describes a two-zone, disconnected immunoassay method. The first zone has non-diffusively bound reagent that binds with a component, for example, an analyte analog bound to, or capable of becoming bound to, a member of a signal producing system. The second zone binds to the component only when the analyte to be tested is present. The distance the component migrates into the second zone is directly related to the concentration of analyte.

U.S. Pat. No. 5,798,273 discloses a lateral flow device that includes a capture zone with immobilized analyte analog and one or more read-out zones to bind labeled analyte-analog.

U.S. Pat. No. 6,001,658 discloses a test strip device with a diffusible, labeled binding partner that binds with analyte, an immobilized analyte, and a detection area containing an immobilized antibody.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as non-woven polyester), for example, to provide increased rigidity to the strip. Zones within each strip may differentially contain the specific binding partner(s) and/or other reagents required for the detection and/or quantification of the particular analyte being tested for, for example, an anti-lipoidal antibody. Thus these zones can be viewed as functional sectors or functional regions within the test device.

In general, a liquid sample (or a sample suspended in a liquid) is introduced to the strip at the proximal end of the strip, for instance by dipping or spotting. A sample is collected or obtained using methods well known to those skilled in the art. The sample containing the anti-lipoidal antibodies to be detected may be obtained from any biological source. Examples of biological sources include blood serum, blood plasma, urine, spinal fluid, saliva, fermentation fluid, lymph fluid, tissue culture fluid and ascites fluid of a human or animal. The sample may be diluted, purified, concentrated, filtered, dissolved, suspended or otherwise manipulated prior to immunoassay to optimize the immunoassay results. The liquid migrates distally through all the functional regions of the strip. The final distribution of the liquid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 25 microns, or more specifically from about 0.1 to 5 microns. In another examples the pore size may vary between from about 0.5 microns to 10 microns. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

Another common feature to be considered in the use of immunoassay devices is a means to detect the formation of a complex between an analyte (such as an anti-lipoidal antibody) and a capture reagent (such as anchor antibody-lipoidal antigen complex or an immobilized lipoidal antigen). A detector (also referred to as detector reagent) serves this purpose. A detector may be integrated into an immunoassay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as, gold-conjugated Protein A for an antibody analyte, or gold-labeled anti-human Ab(Fc) for a human antibody analyte). In other instances, a detector reagent collectively includes an unlabeled first binding partner specific for the analyte and a labeled second binding partner specific for the first binding partner and so forth. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

Preferably, a detector reagent for use in the disclosed methods or devices does not substantially bind to or react with an immobilized lipoidal antigen or an immobilized anchor antibody-lipoidal antigen complex. One of ordinary skill in the art can easily determine combinations of particular detector reagents and particular lipoidal antigen complexes or anchor antibody-lipoidal antigen complexes that will satisfy this preference for the detection of particular analytes. For example, for the detection of human anti-lipoidal antibodies, some non-limiting exemplary combinations include:

| Lipoidal Antigen | Anchor Antibody | Detector Reagent |
|---|---|---|
| CL/L/Ch | human, anti-lipoidal antigen-binding fragment (e.g., Fab) | Protein A, Protein G, or anti-human Ab(Fc) |
| CL/L/Ch | human, anti-cholesterol antigen-binding fragment (e.g., Fab) | Protein A, Protein G, or anti-human Ab(Fc) |
| CL/L/Ch | human, anti-cardiolipin antigen-binding fragment (e.g., Fab) | Protein A, Protein G, or anti-human Ab(Fc) |
| CL/L/Ch | non-human, anti-lipoidal full-length Ab | anti-human Ab (any specificity) |
| CL/L/Ch | non-human, anti-cholesterol full-length Ab | anti-human Ab (any specificity) |
| CL/L/Ch | non-human, anti-cardiolipin full-length Ab | anti-human Ab (any specificity) |
| CL/L/Ch | non-human (mammalian), anti-lipoidal antigen-binding fragment (e.g., Fab) | Protein A, Protein G, anti-human Ab (any specificity) |
| CL/L/Ch | non-human (mammalian), anti-cholesterol antigen-binding fragment (e.g., Fab) | Protein A, Protein G, anti-human Ab (any specificity) |
| CL/L/Ch | non-human (mammalian), anti-cardiolipin antigen-binding fragment (e.g., Fab) | Protein A, Protein G, anti-human Ab (any specificity) |

B. Flow-Through Device Construction and Design

Figure 10:
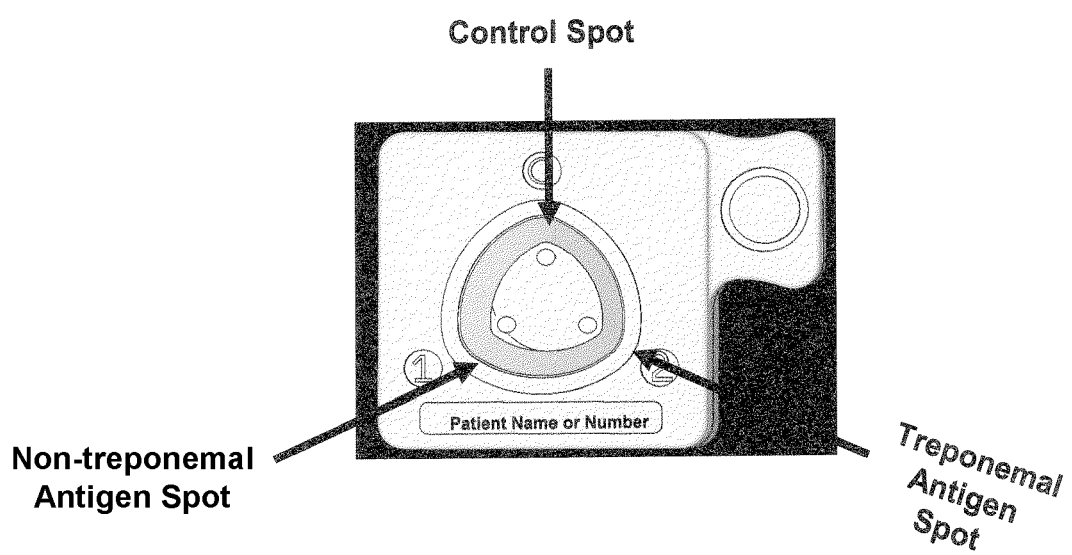
FIG. 10 provides an illustration of an exemplary flow-through device for simultaneous detection of treponemal and non-treponemal antibodies in syphilis. The device is configured to receive a volume of the sample dropwise into a sample introduction port (located in the center of the device).

A flow-through device involves a capture reagent (such as an anchor antibody-lipoidal antigen complex or a lipoidal antigen micelle) immobilized on a solid support, typically, a membrane (such as, nitrocellulose, nylon, or PVDF). Characteristics of useful membrane have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a liquid sample through the membrane. Optionally, following immobilization of a capture reagent, any remaining protein-binding sites on the membrane can be blocked (either before or concurrent with sample administration) to minimize nonspecific interactions. An exemplary physical embodiment of a flow-through device is shown in FIG. 10.

In operation of a flow-through device, a liquid sample (such as a bodily fluid sample) is placed in contact with the membrane. Typically, a flow-through device also includes a sample application area (or reservoir) to receive and temporarily retain a liquid sample of a desired volume. The sample passes through the membrane matrix. In this process, an analyte in the sample (such as an anti-lipoidal antibody) can specifically bind to the immobilized capture reagent (such as anchor antibody-lipoidal antigen complex or an immobilized lipoidal antigen). Where detection of an analyte-capture reagent complex is desired, a detector reagent (such as labeled Protein A, labeled Protein G, or labeled anti-human IgG(Fc)) can be added with the sample or a solution containing a detector reagent can be added subsequent to application of the sample. If an analyte is specifically bound by the capture reagent, a visual representative attributable to the particular detector reagent can be observed on the surface of the membrane. Optional wash steps can be added at any time in the process, for instance, following application of the sample, and/or following application of a detector reagent.

C. Lateral Flow Device Construction and Design

Lateral flow devices are commonly known in the art. Briefly, a lateral flow device is an analytical device having in its essence a test strip, through which flows a test sample liquid that is suspected of containing an analyte of interest. The test liquid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; and 6,368,876; EP 0810436; and WO 92/12428; WO 94/01775; WO 95/16207; and WO 97/06439, each of which is incorporated by reference.

Many lateral flow devices are one-step lateral flow assays in which a biological liquid is placed in a sample area on a bibulous strip (though, non-bibulous materials can be used, and rendered bibulous by applying a surfactant to the material), and allowed to migrate along the strip until the liquid comes into contact with a specific binding partner that interacts with an analyte in the liquid. Once the analyte interacts with the binding partner, a signal (such as a fluorescent or otherwise visible dye) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810; both of which are incorporated herein by reference in their entireties.

Figure 7:
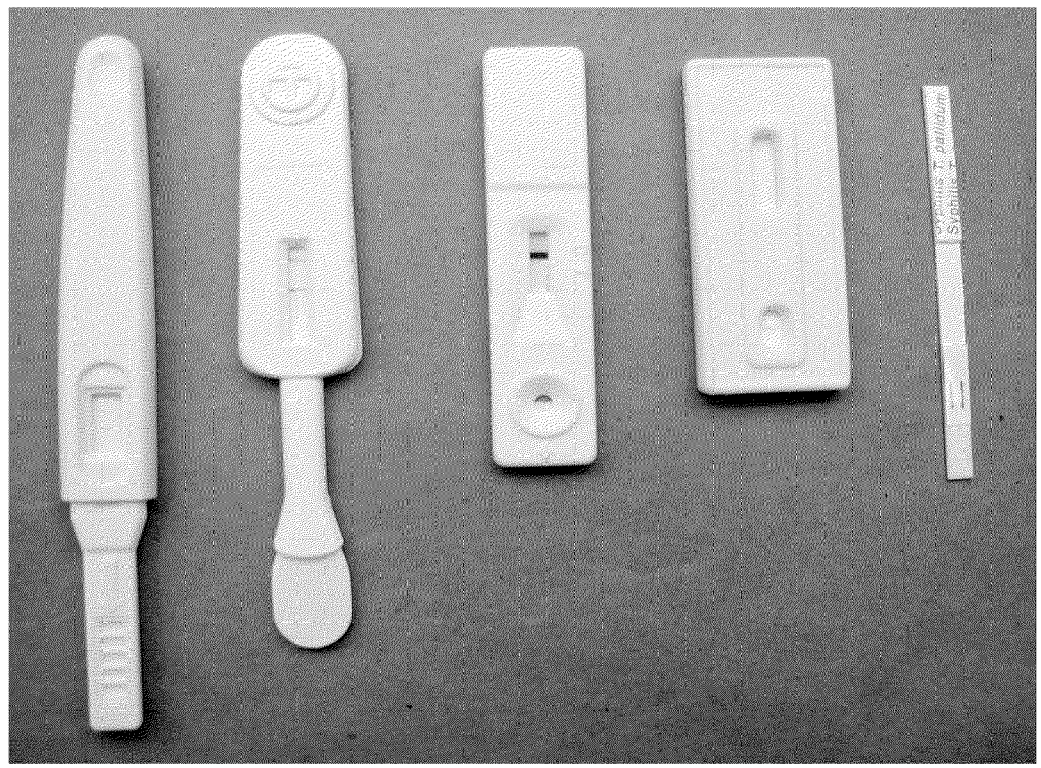
FIG. 7 shows a digital image of five different physical embodiments of lateral flow devices that could be used with the disclosed methods. The device embodiments shown in (A), (B) and (E) are configured so that each may be dipped into, or partially submerged in, the sample or a sample-containing solution. The device embodiments shown in (C) and (D) are configured so as to receive a volume of the sample (or a sample-containing solution) dropwise into a sample introduction port.

Lateral flow devices have a wide variety of physical formats that are equally well known in the art. Any physical format that supports and/or houses the basic components of a lateral flow device in the proper function relationship is contemplated by this disclosure. FIG. 7 shows several examples of lateral flow devices. These examples demonstrate some of the physical embodiments that may be useful in the construction of a lateral flow device.

Figure 8:
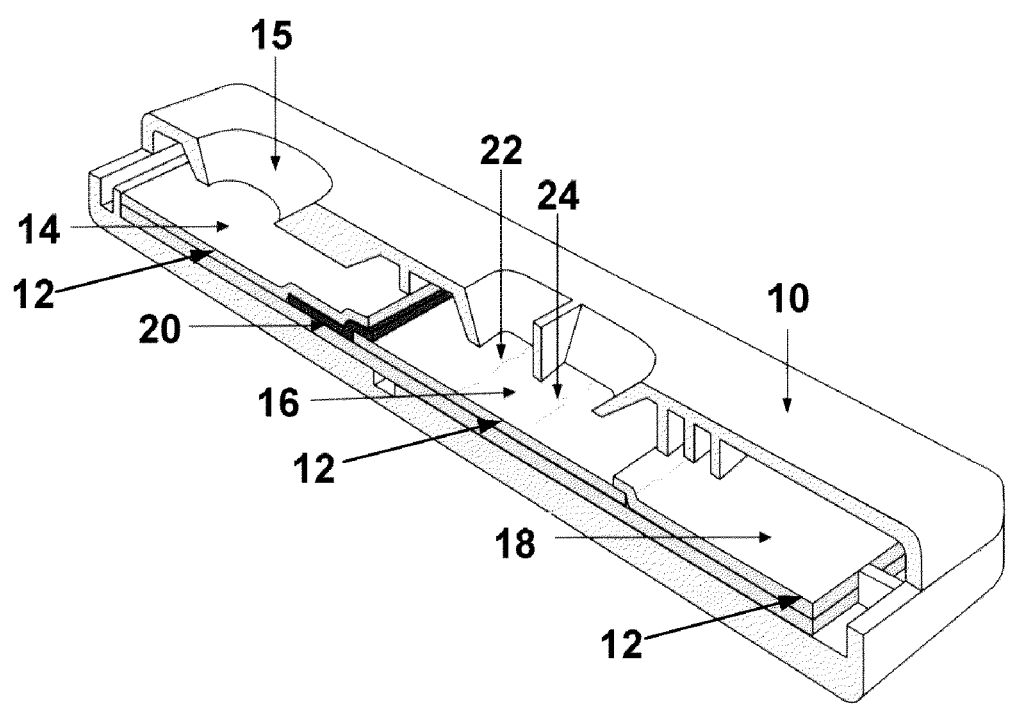
FIG. 8 is a perspective view of a physical embodiment of a lateral flow device, with a portion of the housing broken away to show the basic components of the device and their relationship to each other.

The basic components of a particular embodiment of a lateral flow device are illustrated in FIG. 8, which shows a particular embodiment in which an elongated housing 10 contains a bibulous lateral flow strip 12 that extends substantially the entire length of housing 10. Lateral flow strip 12 is divided into a proximal sample application pad 14 positioned below a sample introduction port 15, an intermediate test result membrane 16, and a distal absorbent pad 18. Flow strip 12 is interrupted by a conjugate pad 20 that contains labeled conjugate (such as gold-conjugated Protein A, gold-conjugated Protein G, gold-conjugated anti-human Ab). A flow path along strip 12 passes from proximal pad 14, through conjugate pad 20, into test result membrane 16, for eventual collection in absorbent pad 18. Selective binding agents (such as an anchor antibody-lipoidal antigen complex) are positioned on a proximal test line 22 in test result membrane 16. A control line 24 is provided in test result membrane 16 slightly distal to test line 22.

In operation of the particular embodiment of a lateral flow device illustrated in FIG. 8, a liquid sample containing an analyte of interest, such as an anti-lipoidal antibody, is applied to the sample pad 14 through the sample introduction port 15. In some examples, the sample may be applied to the sample introduction port 15 dropwise or, less preferably, by dipping the end of the device containing the sample introduction port 15 into the sample. In other examples where a sample is whole blood, an optional developer fluid is added to the blood sample to cause hemolysis of the red blood cells and, in some cases, to make an appropriate dilution of the whole blood sample. From the sample pad 14, the sample passes, for instance by capillary action, to the conjugate pad 20. In the conjugate pad 20, the analyte of interest may bind (or be bound by) a mobilized or mobilizable detector reagent. For example, an anti-lipoidal antibody analyte may bind to a gold-conjugated Protein A detector reagent contained in the conjugate pad. The analyte complexed with the detector reagent may subsequently flow to the test result membrane 16 where the complex may further interact with an analyte-specific binding partner (such as an anchor antibody-lipoidal antigen complex), which is immobilized at the proximal test line 22. In some examples, an anti-lipoidal antibody complexed with a detector reagent (such as, gold-conjugated Protein A, gold-conjugated Protein G, or gold-conjugated anti-human Ab) may further bind to unlabeled, anchor antibody-lipoidal antigen complexes immobilized at the proximal test line 22. The formation of the immunocomplex between anti-lipoidal antibody, labeled (e.g., gold-conjugated) detector reagent, and immobilized anchor antibody-lipoidal antigen complex can be detected by the appearance of a visible line at the proximal test line 22, which results from the accumulation of the label (e.g., gold) in the localized region of the proximal test line 22. The control line 24 may contain an immobilized, detector-reagent-specific binding partner, which can bind the detector reagent in the presence or absence of the analyte. Such binding at the control line 24 indicates proper performance of the test, even in the absence of the analyte of interest.

In another embodiment of a lateral flow device, there may be a second test line located parallel or perpendicular (or in any other spatial relationship) to test line 22 in test result membrane 16. The operation of this particular embodiment is similar to that described in the immediately preceding paragraph with the additional considerations that (i) a second detector reagent specific for a second analyte, such as an anti-*T. pallidum* antibody, may also be contained in the conjugate pad, and (ii) the second test line will contain a second specific binding partner having affinity for a second analyte in the sample. For example, the second test line may contain immobilized treponemal antigens that will specifically bind anti-*T. pallidum* antibodies present in the sample.

Figure 11:
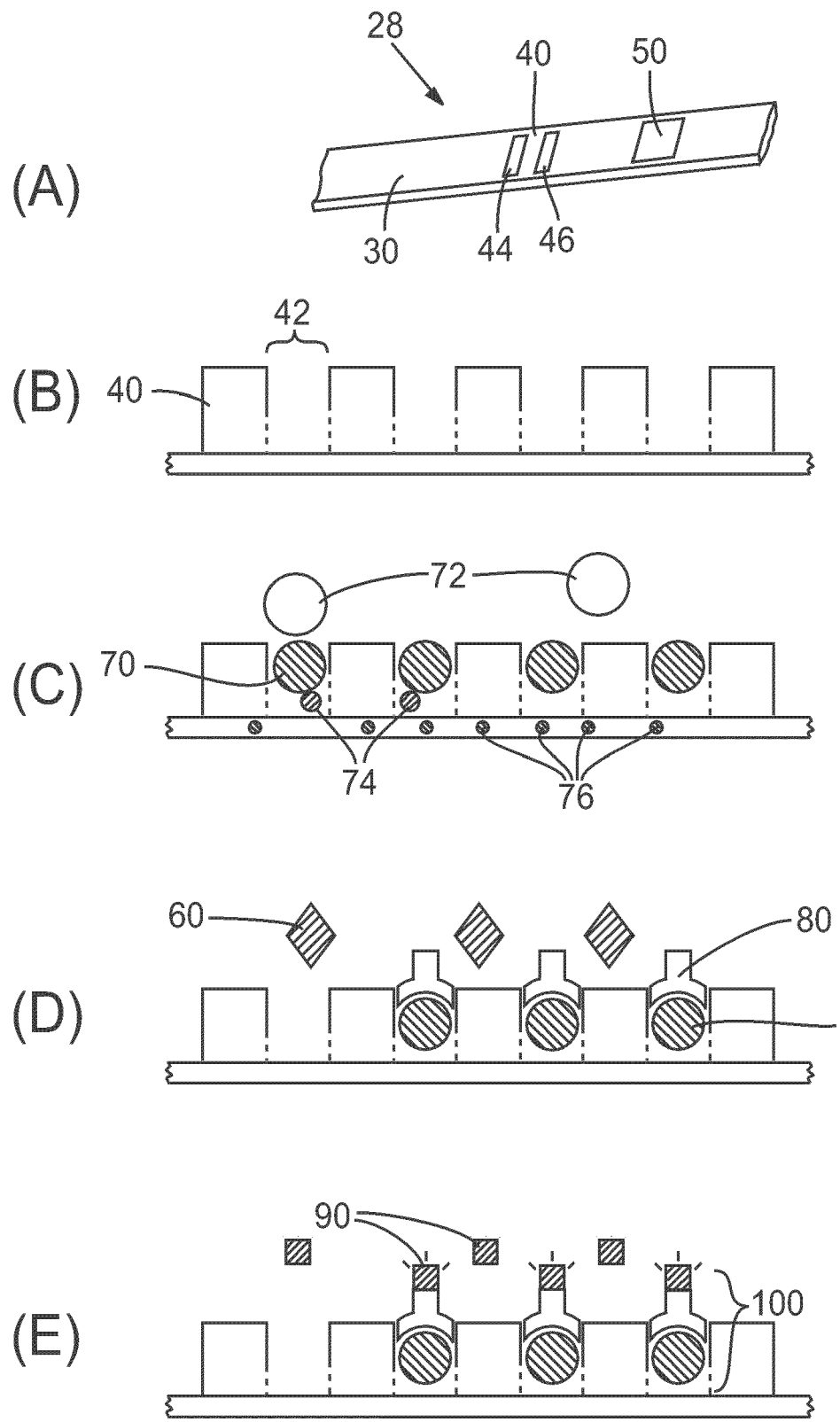
FIG. 11A is a top perspective view of an embodiment of a lateral flow test strip.
FIGS. 11B-11E are enlarged cross-sectional views of a portion of the test strip, illustrating the retention of a lipoidal antigen to a microporous membrane without an anchor antibody. The lipoidal antigen is processed to form lipoidal antigen micelles, which are retained and immobilized within pores of the microporous membrane.

FIGS. 11A-11E are illustrations of an exemplary lateral flow immunoassay test strip 28 incorporating immobilized lipoidal antigen micelles. Specifically, FIG. 11A is an illustration of a top perspective view of an exemplary lateral flow test strip 28 made of a microporous nitrocellulose material. It includes three specific zones: a sample application area 30, a detection zone 40, and an absorbent pad 50. Detection zone 40 contains a proximal test line 44 and a distal control line 46. FIGS. 11B-11E are an enlarged cross-sectional view of a small region of the detection zone 40 through the test line 44. A flow path along test strip 28 passes from sample application area 30 through detection zone 40, for eventual collection in absorbent pad 50.

The detection zone 40 includes one or more capture reagent areas such as positive test line 44 and optional positive control test line 46. Selective capture agents (such as an immobilized lipoidal antigen) 70 are positioned on proximal test line 44 in the microporous test strip 28. Control line 46 is provided in the microporous test strip 28 slightly distal to test line 44. Microporous test strip 28 contains pores of a defined average diameter 42. As shown in FIG. 11B, the pores have an average diameter 42 of about 1 micron. Test strip 28 may also include a mobilization zone, between sample application zone 30 and test line 44, that contains a detector reagent 90 that is mobilized as the sample flows through it, and which binds specifically to an anti-lipoidal antibody 80 to form an analyte-capture-detector complex.

As shown in FIG. 11C, test line 44 may be provided on test strip 28 by applying a lipoidal antigen solution containing micelles of various average diameters 70, 72, 74, and 76, directly to the microporous test strip in a linear distribution along test line 44. In this example, lipoidal antigen micelles 70 of appropriate size are retained and immobilized in the pores of the microporous membrane. Larger micelles 72 and/or smaller lipoidal antigen micelles 74 and 76 migrate through or over the membrane and are not retained in the pores of the microporous membrane thereby migrating to the distal absorbent pad 50.

Operation of the disclosed embodiment of the test strip 28 is illustrated in FIG. 11D. A liquid sample that may contain the analyte of interest, such as an anti-lipoidal antibody 80, is applied to the sample application area 30. The sample may be applied dropwise or, less preferably, by dipping the end of the device containing the sample application area into the sample. In other examples where a sample is whole blood, an optional developer fluid is added to the blood sample to cause hemolysis of the red blood cells and, in some cases, to make an appropriate dilution of the whole blood sample. From the sample application area 30, the sample passes by capillary action through the microporous membrane to detection zone 40 where the analyte of interest such as a (non-treponemal antibody) 80 may bind lipoidal antigen micelle, which is in turn bound by detector reagent 90. For example, an anti-lipoidal antibody may bind to a gold-conjugated Protein A detector reagent contained in the microporous test strip prior to reaching positive test line 44. The analyte complexed with the detector reagent may subsequently flow to the positive test line 44 where the complex may further interact with an analyte-specific binding partner 70 (such as an immobilized lipoidal antigen), which is immobilized at the proximal test line 44. In another embodiment, the analyte 80 may migrate through test strip 28 to capture reagent area 44 where analyte 80 may bind to an immobilized lipoidal antigen 70, whereupon a detector reagent may specifically bind to the immobilized lipoidal antigen-anti-lipoidal antibody complex to generate a detectable positive test line 44.

In the presence of the analyte, an immunocomplex 100 forms that includes an anti-lipoidal antibody 80, labeled (e.g., gold-conjugated) detector reagent 90, and immobilized lipoidal antigen 70. Formation of immunocomplex 100 is detected by the appearance of a visible line at test line 44, which results from the accumulation of a label (e.g., gold) in the localized region of test line 44. Control line 46 may contain an immobilized, detector-reagent-specific binding partner, which can bind detector reagent 90 in the presence or absence of analyte 80. Such binding at control line 46 indicates proper performance of the test strip, even in the absence of the analyte of interest. Samples that do not contain anti-lipoidal antibodies (such as treponemal antibodies (diamonds)) 60 will not immobilize to the detection zone 40 and no positive test line 44 will be observed on the test strip 28. However, in this instance a positive control line 46 will be observed to indicate that the test strip functioned correctly.

Some of the materials that may be useful for the components of a lateral flow device are shown in Table 1. However, one of skill in the art will recognize that the particular materials used in a particular lateral flow device will depend on a number of variables, including, for example, the analyte to be detected, the sample volume, the desired flow rate and others, and can routinely select the useful materials accordingly.

TABLE 1

| Component | Useful Material |
| --- | --- |
| Sample Pad | Glass fiber |
|  | Woven fibers |
|  | Screen |
|  | Non-woven fibers |
|  | Cellulosic filters |
|  | Paper |
| Conjugate Pad | Glass fiber |
|  | Polyester |
|  | Paper |
|  | Surface modified polypropylene |
| Membrane | Nitrocellulose (including pure nitrocellulose and modified nitrocellulose) |
|  | Nitrocellulose direct cast on polyester support |
|  | Polyvinylidene fluoride |
|  | Nylon |
| Absorbent Pad | Cellulosic filters |
|  | Paper |

1. Sample Pad

The sample pad (such as sample pad 14 in FIG. 8) is an optional component of a lateral flow device that initially receives the sample, and may serve to remove particulates from the sample. Among the various materials that may be used to construct a sample pad (see Table 1), a cellulose sample pad may be beneficial if a large bed volume (e.g., 250 $\mu l/cm^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose, nylon and PVDF), and considerations for applying a capture reagent to such membranes have been discussed previously.

3. Conjugate Pad

The conjugate pad (such as conjugate pad 20 in FIG. 8) serves to, among other things, hold a detector reagent. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application. In the particular disclosed embodiment, the detector reagent in conjugate pad 20 is labeled Protein A, Protein G, or anti-human IgG(Fc).

4. Absorbent Pad

The use of an absorbent pad (such as absorbent pad 18 in FIG. 8) in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, see, for example, Table 1. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

D. Combination Devices

Each of the immunoassay devices discussed above (e.g., dipstick, flow-through device or lateral flow device) can be, in some embodiments, formatted to detect multiple analytes by the addition of secondary, tertiary or more capture areas containing capture reagents specific for other analytes of interest. In particular, this disclosure contemplates immunoassay devices that concurrently detect anti-lipoidal antibody and treponemes or anti-treponemal antibodies in liquid samples (such as, human serum). Such combination devices further include a treponemal capture area involving (a) an immobilized treponemal antigen capable of being specifically bound by an anti-*T. pallidum* antibody, or (b) an immobilized anti-*T. pallidum* antibody that specifically binds a mobile treponemal antigen. As used herein, a "treponemal antigen" is an antigen containing at least one antigenic determinant that specifically binds anti-*T. pallidum* antibodies. Numerous treponemal antigens have been described in the art; see, for example, U.S. Pat. Nos. 6,479,248; 6,248,331; 5,681,934; 5,578,456; 4,868,118; and 4,740,467. For instance, polypeptides of at least the following apparent molecular weights have been described as *T. pallidum* antigens: 16-20 kDa, 18 kDa, 18-23 kDa, 25 kDa, 35 kDa, 37 kDa, 37-46 kDa, 38 kDa, 39 kDa, 41 kDa, 43 kDa, 44 kDa, 46 kDa, 47 kDa, 58 kDa, 150 kDa; and 180 kDa (for more particular detail, see U.S. Pat. No. 4,846,118).

Treponemal antigens and anti-*T. pallidum* antibodies are polypeptides; thus, when used as capture reagents, these molecules can be directly adhered to a solid support (such as, nitrocellulose, nylon or PVDF). Nonetheless, it is contemplated that treponemal antigens or anti-*T. pallidum* antibodies can be immobilized (directly or indirectly) on a solid support by any available method.

A detector reagent can be used to detect the formation of a complex between a treponemal capture reagent and treponeme-specific analyte (such as, a treponeme, a treponemal antigen, or an anti-treponemal antibody). In some embodiments, a detector reagent (such as an anti-human Ab(Fc)) can specifically detect a bound treponeme-specific analyte (e.g., a human anti-treponemal antibody) and a bound anti-lipoidal antibody analyte (e.g., a human anti-lipoidal antibody). In other instances, two separate detector reagents for specific detection of a bound treponeme-specific analyte (e.g., anti-treponemal antibody or treponemal antigen) or a bound anti-lipoidal antibody analyte are envisioned.

The operation of an immunoassay device useful for performing concurrent treponemal and non-treponemal tests is substantially similar to devices described elsewhere in this specification. One particular feature of a combination device is that a liquid sample applied to a sample application area is able to contact (e.g., flow to or flow through) each of an anti-lipoidal antibody capture area and to a treponemal capture area.

VI. Kits

Disclosed herein are kits for use in detecting anti-lipoidal antibodies in a sample (such as, a biological sample). Such kits can also be used, for example, in the diagnosis of diseases in which the presence of anti-lipoidal antibodies is symptomatic of the disease (such as, syphilis or lupus). Certain embodiments of the disclosed kits are generally portable and provide a simple, rapid, and/or cost-effective way to detect anti-lipoidal antibodies and/or diagnose disease (such as syphilis) without the need for laboratory facilities, such as in a point-of-care facility.

Kits include one or more immunoassay devices as disclosed herein and a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain, for example, one or more biological samples to be tested, positive and/or negative control samples or solutions (such as, a positive control serum containing anti-lipoidal or treponemal antibodies), diluents (such as, phosphate buffers, or saline buffers), detector reagents (e.g., for external application to a kit device), substrate reagents for visualization of detector reagent enzymes (such as, 5-bromo-4-chloro-3-indolyl phosphate, nitroblue tetrazolium in dimethyl formamide), and/or wash solutions (such as, Tris buffers, saline buffer, or distilled water).

Other kit embodiments include syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain implements useful for introducing samples into a sample chamber of an immunoassay device, including, for example, droppers, Dispo-pipettes, capillary tubes, rubber bulbs (e.g., for capillary tubes), and the like. Still other kit embodiments may include disposal means for discarding a used immunoassay device and/or other items used with the device (such as patient samples, etc.). Such disposal means can include, without limitation, containers that are capable of containing leakage from discarded materials, such as plastic, metal or other impermeable bags, boxes or containers.

In some examples, a disclosed kit will include instructions for the use of an immunoassay device. The instructions may provide direction on how to apply sample to the test device, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify analyte using the test device, such as a standard curve relating intensity of signal or number of signal lines to an amount of analyte therefore present in the sample.

EXAMPLES

The following examples are provided to illustrate certain particular features and/or embodiments. These examples should not be construed to limit the invention to the particular features or embodiments described.

Example 1

Preparation of a USR Lipoidal Antigen Via Centrifugation

This Example describes the preparation of a lipoidal antigen, a USR antigen, which can be attached to a solid support, such as nitrocellulose, using the disclosed methods. Approximately 100 ml of a USR antigen can be prepared as described in this Example; however, those of ordinary skill in the art will appreciate that this described protocol can be scaled upward or downward to produce more or less, respectively, USR antigen. Moreover, unless expressly stated otherwise, all method steps, reactions, etc. in this and the following examples were performed at room temperature (e.g., from about 20° C. to about 25° C.).

Eight (8) ml of VDRL buffered saline (10 grams NaCl, 0.5 ml formaldehyde, 0.093 grams disodium hydrogen phosphate, and 0.170 grams potassium dihydrogen phosphate in 1 liter of distilled water) was added to a 250 ml round, glass-stoppered bottle. Over a period of 40 to 60 seconds, 10 ml VDRL antigen (0.9% cholesterol, 0.03% bovine heart cardiolipin, and about 0.21% lethicin in ethanol) was added directly onto the VDRL buffered saline with continuous rotation of the bottle. Rotation of the bottle was continued for approximately 10 seconds following the addition of the VDRL antigen. Then, 82 ml VDRL buffered saline was added to the reaction mixture. With the top placed on the bottle, the bottle was shaken approximately 30 times over 10 seconds.

Approximately 19 ml aliquots of the shaken mixture were centrifuged in stainless steel tubes in an angle centrifuge (Sorvall SS-3) at room temperature at a relative centrifugal force of approximately 2000×g for 15 minutes (measured from when the centrifuge reached the desired speed). The supernatant liquid was carefully decanted by inverting the tube away from the side containing the sedimented material. After removing the supernatant, the centrifuge tube was inverted and wiped with cotton gauze without disturbing the sediment. The sediment was resuspended with gentle shaking in a volume of resuspending solution (3.72% EDTA, 40% choline chloride (v/v), phosphate buffered saline pH 6.9±0.1) equal to that of the antigen suspension centrifuged (in this case, 19 ml). All resuspended sediments were recombined in a glass-stoppered bottle and gently swirled to mix the antigen preparation. The lipoidal antigen preparation was placed in a refrigerator (from about 2° C. to about 8° C.) for approximately one week to stabilize.

Example 2

Alternative Method for the Preparation of a USR Lipoidal Antigen Via Differential Centrifugation This Example describes the preparation of a lipoidal antigen, a USR antigen, which can be attached to a solid support, such as nitrocellulose, using the disclosed methods. Approximately 1000 ml of a USR antigen can be prepared as described in this Example; however, those of ordinary skill in the art will appreciate that this described protocol can be scaled upward or downward to produce more or less, respectively, USR antigen. Moreover, unless expressly stated otherwise, all method steps, reactions, etc. in this and the following examples were performed at room temperature (e.g., from about 20° C. to about 25° C.).

80 ml of VDRL buffered saline (10 grams NaCl, 0.5 ml formaldehyde, 0.093 grams disodium hydrogen phosphate, and 0.170 grams potassium dihydrogen phosphate in 1 liter of distilled water) was added to the bottom of a 2 liter round, glass-stoppered bottle. Over a period of approximately 60 seconds, 100 ml of synthetic VDRL antigen (0.9% cholesterol, 0.03% bovine heart cardiolipin, and about 0.21% lethicin in ethanol) was added slowly directly onto the VDRL buffered saline while the bottle was continuously rotated at 100 rpm. Then, 820 ml VDRL buffered saline was added to the mixture above. With the top placed on the bottle it was shaken from back to front 30 times over 20 seconds.

The solution was centrifuged at 8000 rpm for one hour at 25° C. The pellet was located and the supernatant was decanted. The pellet was gently resuspended with micelle resuspending solution (USR) to bring the volume to 1000 ml. The supernatant was saved because it contained very small lipoidal antigen micelles. The supernatant was subjected to further centrifugation between 14,000 and 15,000 rpm for one hour at 5° C. and the resulting pellet resuspended to approximately 1 ml with micelle resuspending solution (USR). This differential centrifugation step allowed for the separation of small and large lipoidal antigen micelles over a short period of time.

The pellet resuspension solution (1000 ml) was centrifuged again at 2000 rpm for one hour at 5° C. The pellet was saved for further use. The supernatant containing small lipoidal antigen micelles was further centrifuged at 2000 rpm for one hour at 5° C. The supernatant containing small lipoidal antigen micelles was centrifuged between 14,000 and 15,000 rpm for 1 hour at 5° C. and resuspended to approximately 10 ml with micelle resuspending solution (USR). The desired final concentration was adjusted to 3-4%. The pellet containing large lipoidal antigen micelles was resupended in (USR) solution and sonicated to reduce the size of the lipoidal antigen micelles.

Example 3

Second Alternative Method for the Preparation of a USR Lipoidal Antigen Via Sonication and Filtration This Example describes the preparation of a lipoidal antigen, a USR antigen, which can be attached to a solid support, such as nitrocellulose, using the disclosed methods. Approximately 1000 ml of a USR antigen can be prepared as described in this Example; however, those of ordinary skill in the art will appreciate that this described protocol can be scaled upward or downward to produce more or less, respectively, USR antigen. Moreover, unless expressly stated otherwise, all method steps, reactions, etc. in this and the following examples were performed at room temperature (e.g., from about 20° C. to about 25° C.).

80 ml of VDRL buffered saline (10 grams NaCl, 0.5 ml formaldehyde, 0.093 grams disodium hydrogen phosphate, and 0.170 grams potassium dihydrogen phosphate in 1 liter of distilled water) was added to the bottom of a 2 liter round, glass-stoppered bottle. Over a period of approximately 60 seconds, 100 ml of synthetic VDRL antigen (0.9% cholesterol, 0.03% bovine heart cardiolipin, and about 0.21% lethicin in ethanol) was added slowly directly onto the buffered saline while the bottle was continuously rotated at 100 rpm. Then, 820 ml buffered saline was added to the mixture above. With the top placed on the bottle it was shaken from back to front 30 times in 20 seconds.

The mixture was centrifuged at 7000 rpm for one hour at 25°. The pellet was located and the supernatant liquid was decanted. The pellet was gently resuspended with micelle resuspending solution (USR) to a 1000 ml volume.

Using a Misonix S-400 sonicator system with a Titanium probe, the 1000 ml of USR antigen was sonicated at 40 KHz for 15 to 20 minutes, followed by centrifugation at 2000 rpm for 30 minutes. The supernatant containing small lipoidal antigen micelles was decanted, and the precipitate containing large lipoidal antigen micelles was saved for further sonication. The large lipoidal antigen micelles were resuspended to approximately 20% concentration in USR buffer. The large lipoidal antigen micelles were sonicated at 40 KHz for approximately 15 minutes. This step was repeated until the large lipoidal antigen micelles were reduced to the appropriate size.

Using a Millipore™ or equivalent filter assembly, the sonicated small lipoidal antigen micelles were filtered by gravity through a 5 micron membrane, then filtered through a 3 micron membrane, a 1.8 micron membrane, a 0.8 micron membrane and a 0.65 micron membrane. The microporous membrane used in construction of a lateral flow or flow-through device was determined by reactivity of the sonicated small lipoidal antigen micelles with the pores of the microporous membrane, for example by determining the binding affinity of the lipoidal antigen micelles.

Example 4

Ammonium Sulfate Fractionation of *T. pallidum*-Infected Human Serum

This Example describes one method for separating an immunoglobulin-containing fraction from serum. The method of this Example (as well as other immunoglobulin isolation methods that are commonly known in the art) can be used to partially purify immunoglobulins from any source of blood serum, including serum from non-human subjects (such as, rabbits).

Serum from human patients infected with *T. pallidum* (referred to throughout this and the following examples as "hyperimmune antiserum") was obtained from Biomedical Resources (Hatboro, Pa.). A desired volume of hyperimmune antiserum was placed in a container that held more than twice the volume of serum. With stirring, an amount of 70% saturated ammonium sulfate equal to the volume of serum was slowly added dropwise to the serum. This mixture was stirred for approximately 4 hours at room temperature prior to centrifugation at approximately 3000 rcf for 30 minutes. Following centrifugation, the supernatant was discarded and the precipitated immunoglobulin-containing fraction was resuspended in a volume of distilled water equal to the original volume of serum. Then, an equal amount of 70% saturated ammonium sulfate solution was added dropwise to the resuspended immunoglobulin-containing fraction with stirring, the mixture was centrifuged, the supernatant decanted, and the precipitate resuspended as above. This procedure was then repeated one more time. The final immunoglobulin-containing precipitate was resuspended with distilled water to one-tenth the original serum volume. The resuspended immunoglobulin-containing fraction was dialyzed against three 100× volumes of 0.85% sodium chloride pH 8.0 overnight at 2-8° C. Total protein concentration in the dialysis retentate was determined by the Bio-Rad™ Bradford Protein Assay according to the manufacturer's instructions.

Example 5

Purification of IgG Using a Protein A Affinity Column

IgGs were isolated from the immunoglobulin-containing fraction of Example 2 using Protein A agarose chromatography. As is known in the art, Protein A specifically binds to the Fc region of IgG from a variety of mammalian species.

A buffer reservoir containing 1000 ml of 20 mM sodium phosphate buffer, pH 7.4 ("phosphate buffer") was connected to a 10 ml Protein A Sepharose CL-4B column (Pharmacia). The column was washed with 200 ml of the phosphate buffer, and the pH of the eluant measured. The column was not loaded with the immunoglobulin-containing sample until the pH of the eluant was in the range of 7.3±0.2.

After disconnecting the buffer reservoir, the immunoglobulin-containing dialysis retentate from Example 2 was applied to the column taking care not to disturb the surface of the column matrix. Then, 20 ml of phosphate buffer was added to the column, the buffer reservoir was reattached to the column, and fractions were collected using a fraction collector loaded with 80-12×125 mm diameter tubes. The absorbance at 280 nm of the column eluant was monitored. When the absorbance at 280 nm of the eluant returned to baseline (indicating the substantially complete elution of non-specific protein), a second buffer reservoir containing 500 ml of 100 mM glycine pH 2.7 was connected to the column. Again, fractions were collected while monitoring the absorbance of the eluant at 280 nm. All fractions eluted in the glycine buffer having an $absorbance_{280\ nm}$ of 0.1 or greater were combined. Such fractions included proteins specifically bound by Protein A, i.e., IgGs, that were present in the *T. pallidum*-infected human serum. The pH of the combined solution was adjusted to 7.2±0.2 using 2.0 M Tris buffer, and total protein concentration was determined as described previously.

Example 6

Specific Binding of Protein A-Purified IgG to USR Antigen in Solution

The endpoint titer of the Protein A-purified IgGs obtained as described in Example 3 was determined. Serial dilutions of the IgG sample (from 1:2 to 1:512) in 0.9% saline were made. Fifty (50) μl of each dilution was placed in each of 10 circles (14 mm) on a 2×3 inches glass slide.

The USR antigen, prepared as described in Example 1, was gently resuspended and drawn into a dispensing needle and syringe in a vertical position. Several drops were dispensed and discarded to clear the needle of air. Then, 1 free-falling drop (approximately 22 μL) of antigen suspension was added to each circle containing IgG. The slide was placed on the mechanical rotator for 4 minutes at 180±2 rpm. When performing this test in a dry climate where evaporation may be a problem, it may be advantageous to place the slides under a moist humidifying cover during the rotation step. Immediately after rotation, the slide was viewed microscopically using 10× oculars and a 10× objective to determine in which reactions flocculation occurred. The IgG titer was determined to be the highest dilution that gives a weak (or weakly) positive reaction.

An original volume of Protein A-purified IgG sample was diluted in a first dilution volume of phosphate buffered saline pH 7.2±0.2 ("PBS") to an effective antibody titer of 1:2048. Thus, in one situation where the endpoint titer of the sample was 1:32, one volume of sample was diluted with 64 volumes of phosphate buffered saline pH 7.2±0.2 ("PBS") (In other examples, a serum having a 1:16 endpoint titer will be diluted with 128 volumes PBS, and a serum having a 1:64 endpoint titer will be diluted with 32 volumes PBS, etc.). Then, a volume of USR micelle (prepared as described in Example 1) equal to the original volume of purified IgG was added to the diluted IgG sample with gentle mixing. The mixture was allowed to settle at 2-8° C. for several days until the supernatant cleared. Then, the supernatant was removed and replaced with a volume of PBS equal to the first dilution volume (e.g., 64 volumes of PBS in the above-described situation). The foregoing steps were repeated until the supernatant was clear. After removing the final supernatant, the volume of precipitated material (containing USR micelle-antibody (IgG) complexes; also referred to as IgG-coated micelles) was measured with a cylinder, and the protein concentration of the IgG-coated micelle was determined by the Bradford method.

Example 7

Preparation and Isolation of Fab Fragments

Protein A-purified IgG (prepared as described in Example 3) was concentrated to approximately 20 mg/ml using a Centricon™ centrifugal filter (Millipore) and dialyzed against 2×1000 ml Sample Buffer (20 mM sodium phosphate, 10 mM EDTA, pH 7.0).

Papain immobilized on 6% cross-linked beaded agarose in a 50% slurry in 50% glycerol, 0.1 M sodium acetate (pH 4.4) and 0.05% sodium azide (Pierce) was mixed by inversion or gentle shaking to obtain an even suspension. Then, 2.5 ml of the slurry was added to a glass test tube or other suitable reaction vessel. To equilibrate the gel, 20 ml of freshly prepared Digestion Buffer (20 mM sodium phosphate, 10 mM EDTA, 20 mM cysteine-HCl, pH 7.0) was added the slurry. Then, the gel was separated from the buffer by centrifugation, and this procedure was repeated with another 20 ml of Digestion Buffer. The equilibrated gel was resuspended in 2.5 ml of Digestion Buffer.

Protein A-purified IgG (2.5 ml of a 10 mg/ml solution) was diluted with 2.5 ml of Digestion Buffer. The IgG solution was add to the tube or vessel containing the immobilized papain, and the mixture was incubated from five hours to overnight in a shaker water bath at 37° C. at high speed. A constant mixing of the gel was maintained during the incubation.

Following the incubation, 7.5 ml of 10 mM Tris-HCl, pH 7.5 was added to the reaction mixture, and mixture was separated by centrifugation at 300 rpm for 25 minutes. The supernatant (which contains immunoglobulin fragments) was removed from the sedimented immobilized papain.

The supernatant was run on a Protein A column as described in Example 3. As shown in FIG. 1, two protein peaks were recovered. Peak I, which did not specifically bind Protein A, was the Fab fraction of immunoglobulin fragments, and Peak II, which did specifically bind Protein A, was the Fc fraction. The protein concentrations of Fab and Fc fractions were determined as previously described.

Example 8

Polyacrylamide SDS Gradient Gel Analysis of Immunglobulin-Containing Samples

This Example illustrates the protein content of various samples produced in Examples 2, 3 and 5. A Bio-Rad™ pre-cast 10-20% linear polyacrylamide gradient gel with 4% stacking gel was used to separate, by size, the protein bands present in the ammonium sulfate immunoglobulin fraction (see Example 2), Protein A peaks I and II (see Example 3), Protein A-purified IgG before and after papain digestion (see Example 5), and IgG peaks I (Fab fraction) and II (Fc fraction) after papain digestion (see Example 5).

Samples (2.5 µg/µl) were diluted 1:1 in Laemmli sample buffer (62.5 mM Tris-HCl, 2% SDS, pH 6.8, 2% SDS and 25% glycerol (with no β-mercaptoethanol)). Samples were heated and loaded in the respective wells. The tank buffer was Tris-glycine-SDS (25 mM Tris-HCl, pH 8.3, 192 mM glycine, 0.1% SDS). The gel was run for 45 minutes at 200 volts. Following three washes with $H_2O$, the gels were stained for 30 minutes with Pierce Gel Code Blue™ and then cleared by repeated washing with water.

Figure 2:
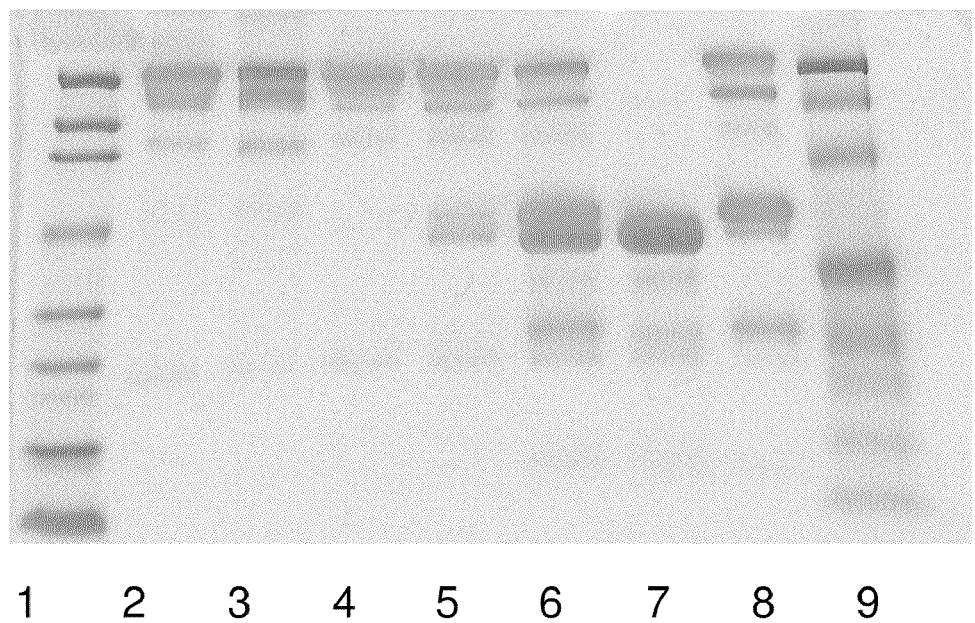
FIG. 2 shows a digital image of an SDS gradient gel. Lanes (1) molecular weight standards (from top: 203, 135, 83, 41, 31, 17, and 7 kD); (2) ammonium sulfate precipitate from human syphilitic serum; (3) ammonium sulfate precipitated proteins not retained by Protein A (peak I); (4) Protein A-purified IgG from ammonium sulfate precipitate (peak II); (5) Protein A-purified IgG before papain digestion; (6) Protein A-purified IgG after papain digestion; (7) proteins from papain IgG digestion that were not retained by Protein A (peak I) (predominantly Fab fragments); (8) Protein A-retained proteins from papain IgG digestion (including Fc fragments); and (9) molecular weight standards (from top: 207, 116, 98, 55, 37, 30, 20 and 7 kD).

As shown in FIG. 2, the ammonium sulfate-precipitated fraction of human hyperimmune (syphilitic) serum (lane 2) contained a mixture of predominantly high molecular weight protein bands. As shown in FIG. 2, lane 4, a relatively pure IgG fraction was bound by and eluted from a Protein A column. Papain digestion of the Protein A-purified IgG produced a mixture of proteins (lane 6), which were separable into two protein populations by fractionation over a Protein A column. FIG. 2, lane 7 shows that one predominant papain-digested IgG fragment of approximately 54 kD was not retained by the Protein A column. This apparent molecular weight is the expected size of Fab fragments. There were substantially no higher molecular weight protein bands (representing, for example, $Fab_2$ or Fc fragments or undigested IgG) observed in lane 7. Proteins having the expected molecular weights of Fc fragments and undigested IgG were retained by the Protein A column (lane 8).

Example 9

Protein a Colloidal Gold Conjugate does not Detect Fab Fragments

One (1) µl of the papain digestion fractions of IgG (prepared as described in Example 5) were spotted on a 5 mm×4 cm nitrocellulose membrane and dried overnight. One hundred (100) µl of 1% casein in 10 mM phosphate buffer with 0.25M sodium chloride, pH 7.4 were place into corresponding wells of a microtiter plate. Two (2) µl of Protein A conjugated to colloidal gold were mixed into each well and the corresponding strips were placed into each well.

Figure 3:
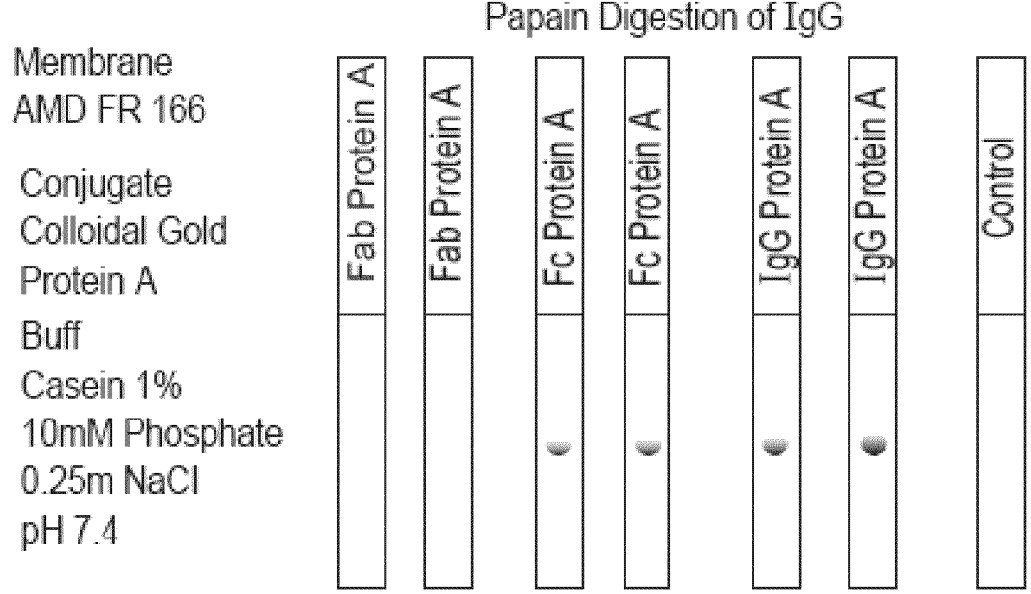
FIG. 3 shows a series of nitrocellulose dipsticks prepared as described in Example 7. The dipsticks were spotted with IgG or Fab or Fc fragments as indicated, and later dipped into a solution containing gold-conjugated Protein A.

As shown in FIG. 3, colloidal gold Protein A conjugate detected the IgG and Fc fractions but not the Fab fractions.

Example 10

Determination of a Useful Amount of Fab to Attach to USR Micelle

Fab fragments prepared as described in Example 5 were diluted in PBS to 1000 µg/µl, 100 µg/µl, 10 µg/µl, 1 µg/µl, 100 ng/µl and 10 ng/µl. Each Fab fraction dilution was mixed with an equal volume of a USR micelle solution prepared as described in Example 1. One (1) µl of this Fab-USR micelle mixture was spotted on a 5 mm×4 cm nitrocellulose membrane and dried overnight at room temperature.

A human antiserum (which was reactive in the RPR test at a 1:64 dilution) was diluted 1:400 in a buffer consisting of 1% casein, 10 mM phosphate, 0.25M sodium chloride pH 7.4. A similarly diluted RPR-non-reactive human serum was used as a negative control. One hundred (100) µl antiserum (or non-reactive serum) and 2 µl colloidal gold Protein A were combined in each of several wells of a microtiter plate. A single nitrocellulose strips containing dried Fab-reacted lipoidal antigen was placed into each well at room temperature for a time sufficient for the components placed in the wells to migrate along the membrane to the location where the Fab-USR micelle mixture was spotted.

Figure 4:
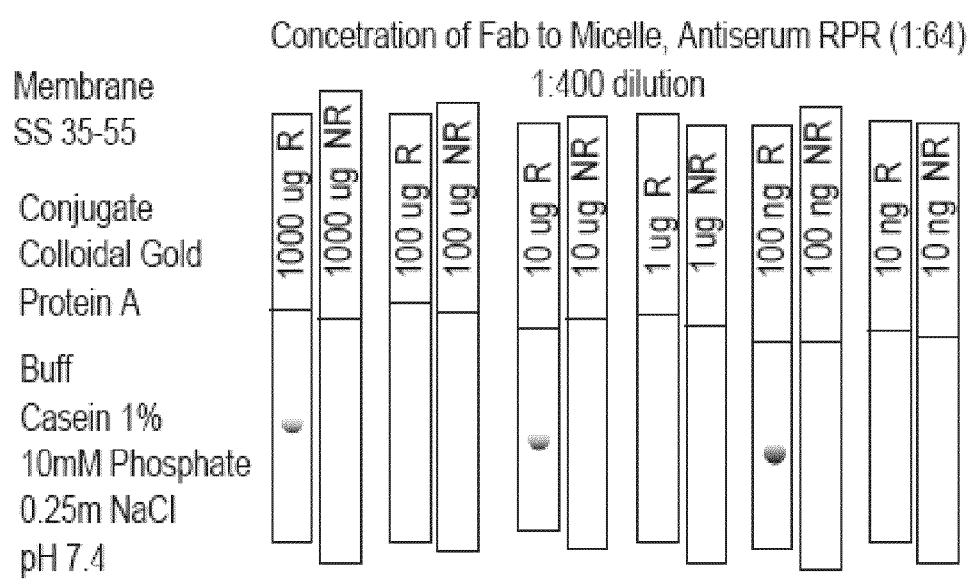
FIG. 4 shows a series of nitrocellulose dipsticks prepared as described in Example 8. The dipsticks were spotted with a USR antigen coated with the indicated amount of Fab fragment, and later dipped into a solution containing gold-conjugated Protein A and reactive syphilis serum (R) or non-reactive syphilis serum (NR).

As shown in FIG. 4, nitrocellulose strips having 1000, 10 or 0.1 µg Fab bound to USR antigen gave a positive reaction with RPR-reactive (R) human serum. No reaction was observed for any of the samples containing RPR-non-reactive (NR) serum.

This Example demonstrates that, at least, from about 100 ng to about 1 mg Fab fragments (such as from about 100 ng to about 450 ng) can be reacted with a USR antigen preparation (see Example 1) to facilitate attachment of the lipoidal antigen to a nitrocellulose membrane without substantial adverse effect on the reactivity of the USR antigen with serum antilipoidal antibodies in an immunoassay assay (such as, test strips, and flow-through and/or lateral flow devices). One non-limiting useful amount of Fab fragment to use as described in this Example is about 10 µg.

Example 11

Determination of a Useful pH for Conjugation of Affinity Purified Rabbit Anti-Human IgG (Fc) to Colloidal Gold This Example illustrates a representative method for determining a useful pH for conjugating affinity purified rabbit anti-human IgG (Fc) (Rockland, Gilbertsville, Pa.) with colloidal gold. The rabbit anti-human IgG (Fc) specifically binds only the Fc portion of human IgG, and does not bind to the Fab or other non-Fc regions of a human IgG. Antibodies with this specificity may also be referred to as "anti-human Fc." Colloidal gold preparations such as those described in this and other examples can be used as detector reagents in disclosed immunoassays (including, for example, test strips, and flow-through and/or lateral flow devices).

Approximately 25 ml of 10 mM phosphate buffer was placed in a 50 ml beaker, and adjusted to pH 5.0 with 0.2 M phosphoric acid. Two 0.5 ml aliquots of the buffer at pH 5.0 were transferred to two 12×75 mm test tubes, one labeled "test" and the other labeled "control." Then, the pH of the phosphate buffer remaining in the beaker was sequentially adjusted to 5.5, 6.0, 6.5, 7.0, 7.5, 8.0, 8.5, 9.0, 9.5, and 10.0 using 0.2 M potassium carbonate. At each pH, two 0.5 ml aliquots were transferred to a "test" and "control" test tube as described for the pH 5.0 sample. Then, 30 µg of affinity purified rabbit anti-human IgG (Fc) was added to each of the "test" and "control" tubes, and the tube contents were mixed well. Approximately 25 ml of 40 nm colloidal gold (1% solution) (British Biocell International, London, England) was placed in a separate 50 ml beaker, and a series of "control" and "test" colloidal gold samples at pH 5.0, 5.5, 6.0, 6.5, 7.0, 7.5, 8.0, 8.5, 9.0, 9.5, and 10.0 was produced as described above.

One (1) ml of colloidal gold at each pH was added to the "test" and "control" solutions having the corresponding pH. The gold/rabbit anti-human IgG (Fc) solutions were mixed well, and incubated for 20 minutes at room temperature. Then, 200 µl of 2M NaCl was added to the set of tubes labeled "test" and 200 µl of distilled water was added to the set of tubes labeled "control." The contents of both sets of tubes were allowed to incubate for 30 minutes at room temperature.

The optical density at 580 nm ($OD_{580}$) of each "test" sample was read against the corresponding "control" sample. The pH of the sample with the lowest $OD_{580}$ was determined to be a favorable pH for formation of a gold conjugate preparation. Colloidal gold particles have a negatively charged surface due to the layer of negative ions adsorbed onto the gold particle surface during the manufacturing process. Proteins, such as IgG will be attracted to negatively charged gold particles through ionic, hydrophobic, and dative interactions. These interactions are believed to underlie the formation of colloidal gold-protein conjugates. At the pI of a protein conjugated to a gold particle (i.e., the pH where the protein has a net zero charge), the conjugate will be the most stable.

The addition of NaCl to unconjugated colloidal gold particles will disrupt the layer of negatively charged ions adsorbed to the gold's surface. As a result, the gold particle will dissociate and ultimately release gold ions (i.e., $Au^+$) into solution. The free gold ions may be measured at $OD_{580}$. In contrast, a protein-gold conjugate is resistant to disruption by NaCl at the pI of the protein component of the conjugate. Accordingly, the pH of the sample with the lowest $OD_{580}$ is a useful pH at which to perform gold conjugation reactions to obtain a stable gold conjugate.

Figure 5:
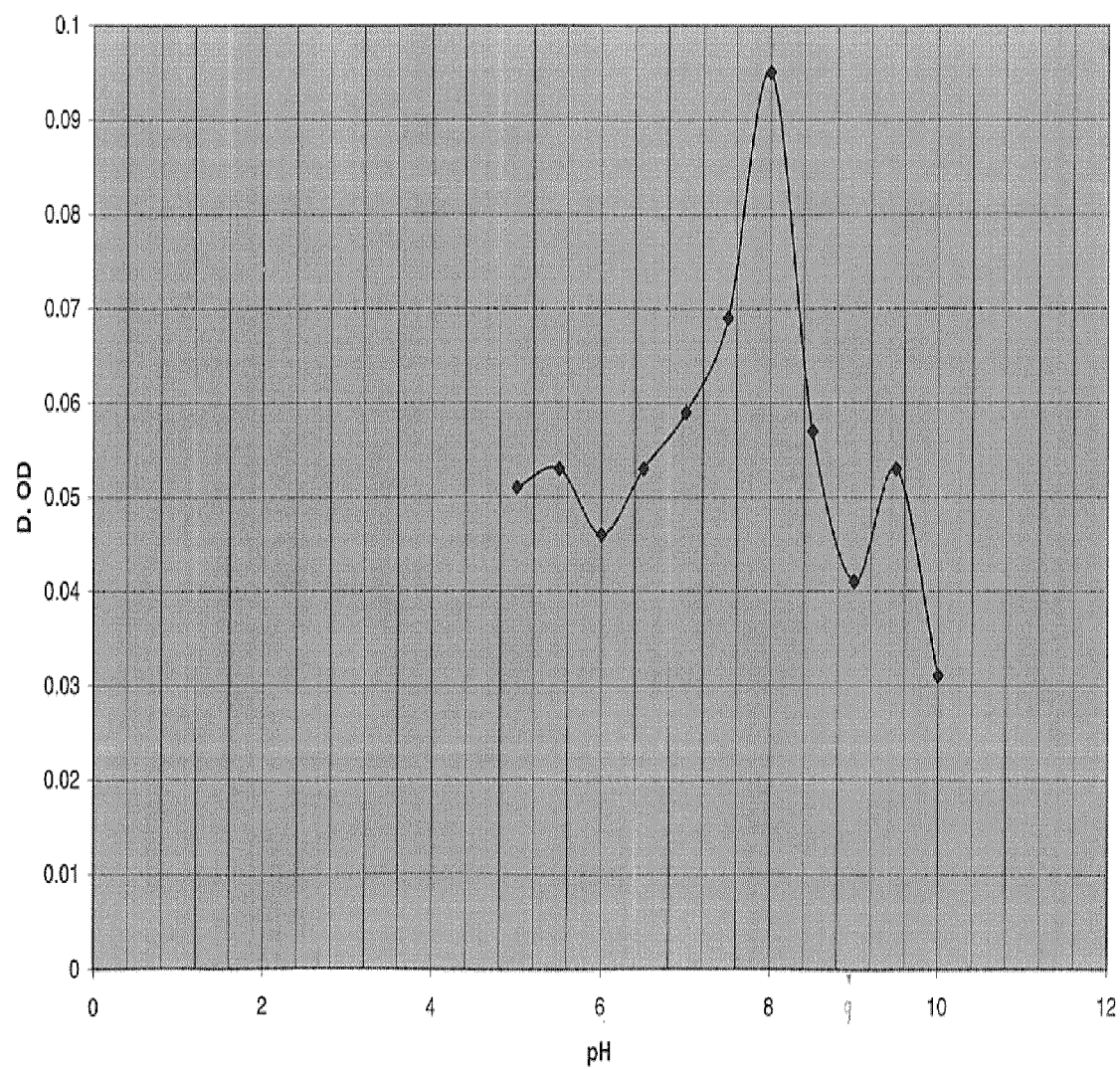
FIG. 5 is a graph of $OD_{580}$ for mixtures of rabbit anti-human IgG (Fc) with colloidal gold as a function of pH. As described in Example 9, a useful pH at which to obtain a stable gold conjugate for these reactants is the pH corresponding to the lowest $OD_{580}$.

As shown in FIG. 5, a useful pH for conjugation of 30 µg rabbit anti-human IgG (Fc) with to 10 µg colloidal gold (i.e., 1 ml of a 1% solution) is approximately pH 9.5. The method described in this Example is broadly applicable to any number of other proteins that may be conjugated to gold for use in a disclosed immunoassay (such as, Protein A or Protein G). In addition, it is believed that the described reactions are scalable to other amounts of protein and gold conjugate.

Example 12

Determination of a Useful Protein Concentration for Colloidal Gold Conjugation

This Example illustrates an exemplary method for determining a useful protein concentration for conjugation reactions with colloidal gold. Colloidal gold preparations such as those described in this and other examples can be used as detector reagents in disclosed immunoassays (including, for example, test strips, and flow-through and/or lateral flow devices).

One-half (0.5) ml of 10 mM phosphate buffer (adjusted to the pH giving the lowest $OD_{580}$ as described in Example 9) was added to 2 sets of 5 tubes. One set of tubes was labeled "test" and the other set was labeled "control." Thirty (30) µg, 20 µg, 10 µg, 5 µg, or 2.5 µg of rabbit anti-human IgG (Fc) was then added to each in the series of tubes, and mixed well. One (1) ml of 40 nm colloidal gold (1% solution adjusted to the same pH as the phosphate buffer) was added to each tube. The samples were incubated for 20 minutes at room temperature. Then, 200 µl of 2M NaCl was added to the samples labeled "test" and 200 µl of distilled water was added to the samples labeled "control." Following incubation for 30 minutes at room temperature, the $OD_{580}$ of the test samples were read against the corresponding control samples. The lowest concentration of rabbit anti-human IgG (Fc) producing the lowest $OD_{580}$ indicates a useful concentration (or concentration range) for formation of a protein-gold conjugate preparation.

In this Example, the lowest concentration of rabbit anti-human IgG (Fc) producing the lowest $OD_{580}$ represents the concentration where a useful amount of rabbit anti-human IgG (Fc) was associated with gold particles. Higher concentrations of rabbit anti-human IgG (Fc), although useful, are less preferred because excess rabbit anti-human IgG (Fc) may form weaker associations with the gold particles, for example, by layering upon a layer of rabbit anti-human IgG (Fc) molecules that previously associated with the gold particles.

Figure 6:
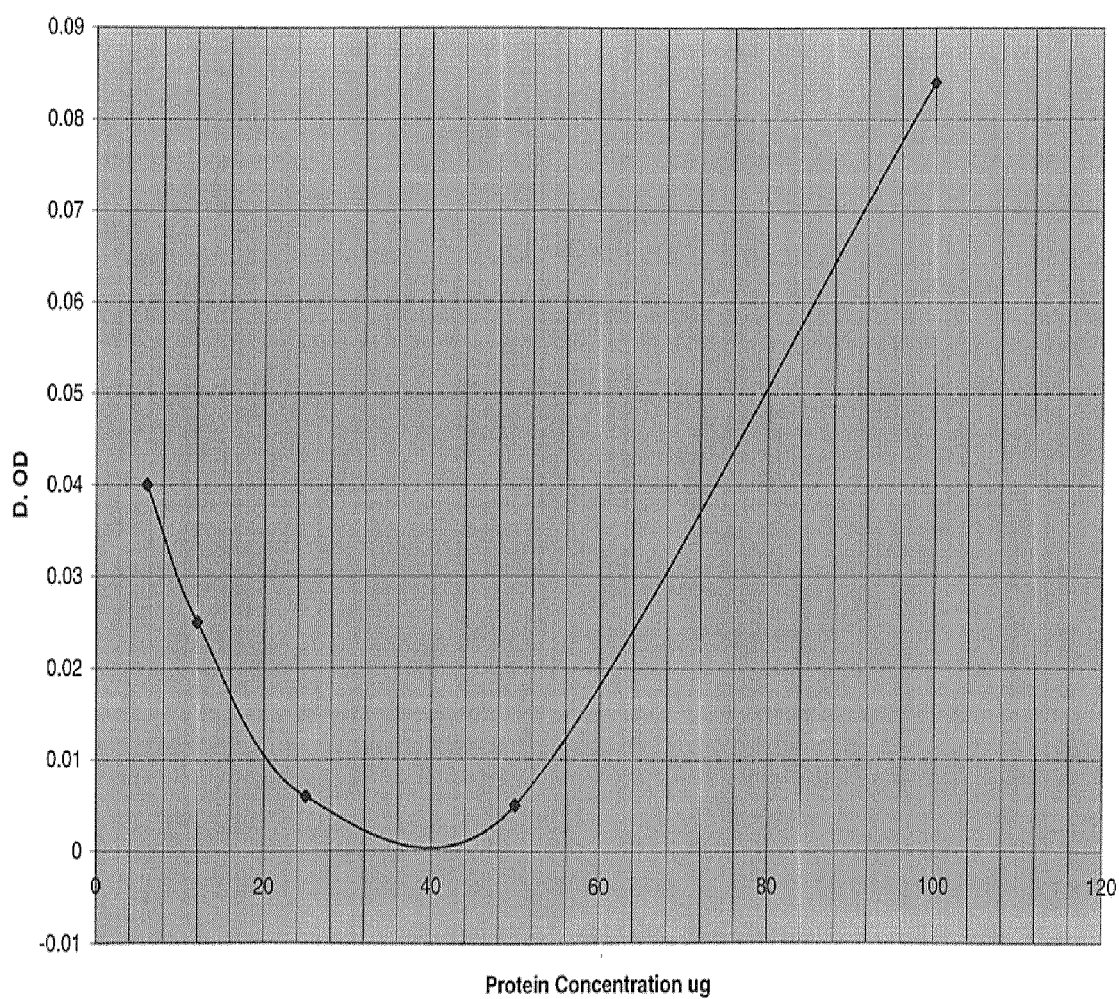
FIG. 6 is a graph of $OD_{580}$ for mixtures of rabbit anti-human IgG (Fc) with colloidal gold as a function of rabbit anti-human IgG (Fc) concentration. As described in Example 10, the protein concentration producing the lowest $OD_{580}$ represents a useful concentration of rabbit anti-human IgG (Fc) to associated with gold particles.

As shown in FIG. 6, approximately 30 µg is a useful amount of rabbit anti-human IgG (Fc) to conjugate to 10 µg colloidal gold (i.e., 1 ml of a 1% solution). The method described in this Example is broadly applicable to any number of other proteins that may be conjugated to gold for use in a disclosed immunoassay (such as, Protein A or Protein G). In addition, it is believed that the described reactions are scalable to other amounts of protein and gold conjugate.

A. Preparation of a Gold Conjugate "Mini-Preparation"

A rabbit anti-human Fc gold conjugate mini preparation was prepared by adding 5 ml of 10 mM borate buffer to an amount of rabbit anti-human IgG (Fc) necessary to achieve a useful protein concentration (such as, 30 µg) as described above. This protein solution was then adjusted to a useful pH (such as, pH 9.5) as also described above. Ten (10) ml of 40 nm colloidal gold (1% solution adjusted to the useful pH) was added to the pH-adjusted protein solution with thorough mixing. The mixture was incubated for 20 minutes at room temperature. Then, 1.6 ml of 10% casein was added to a final concentration of 1% casein, and the incubation continued an additional 20 minutes at room temperature. The reaction mixture was centrifuged at 6500×g for 10 minutes, and the supernatant was removed and discarded. The pellet was resuspended in 0.5 ml of resuspension buffer (150 mM NaCl, 20 mM Trizma base, 10% sucrose, 5% Trehalose, 0.1% casein, 0.05% sodium azide).

The resuspended pellet containing gold conjugated rabbit anti-human IgG (Fc) may be used for a variety of purposes, including without limitation, as a detector reagent for human anti-lipoidal antibodies in a lateral flow device.

Example 13

Detection of Anti-Lipoidal Antibodies in Human Serum

This Example demonstrates that anti-lipoidal antibodies in syphilitic serum may be detected by using a nitrocellulose immobilized Fab-USR antigen complex capture reagent in concert with a mobile rabbit anti-human IgG (Fc) or Protein A gold conjugate detector reagent.

One (1) µl of the Fab-USR antigen complex was applied to separate nitrocellulose membranes and allowed to dry overnight at room temperature as described in Example 8. A colloidal gold conjugate was prepared as described in Example 10. Reactive human syphilitic sera and a non-reactive (non-syphilitic) human serum were diluted 1:100, 1:200 or 1:400 in 1% casein, 10 mM phosphate, 0.5M sodium chloride pH 7.4. One hundred (100) µl of each serum dilution was placed in an appropriate number of separate wells of a microtitre plate. Two (2) µl of gold-conjugated Protein A (prepared in a manner analogous to Example 10) was then added to each well. One nitrocellulose strip containing immobilized Fab-USR antigen complex capture reagent was then placed into each well containing the antibody and detector reagent solutions. The solution in the wells flowed up the strip by capillary action.

As shown in Table 2, many of the sixty reactive human syphilitic sera reacted with the immobilized Fab-USR antigen preparations. A positive reaction was characterized by a visible dot of various shades of intensity, from very faint (VF), faint (F), weak (W) and strong (S). No visible reaction was indicated by "N." There was no reaction observed for the non-reactive (non-syphilitic) human serum at any tested serum dilution.

TABLE 2

Reactivity of Immobilized Lipoidal Antibody with Human Syphilitic Sera

| | | Serum Dilutions | | |
|---|---|---|---|---|
| Serum No. | RPR Titer[a] | 100 | 200 | 400 |
| 1 | R4 | VF | VF | N |
| 2 | R8 | N | VF | F |
| 3 | R2 | N | N | N |
| 4 | R16 | VF | N | W |
| 5 | R32 | S | S | S |
| 6 | NR | N | N | N |
| 7 | R64 | VF | F | W |
| 8 | R128 | S | S | S |
| 9 | R4 | VF | VF | N |
| 10 | R64 | W | W | W |
| 11 | R256 | S | S | S |
| 12 | NR | N | N | N |
| 13 | R512 | S | S | S |
| 14 | R16 | VF | W | W |
| 15 | R8 | W | W | F |
| 16 | R1024 | S | S | S |
| 17 | NR | N | N | N |
| 18 | R512 | S | S | S |
| 19 | R64 | F | W | W |
| 20 | R256 | S | S | S |
| 21 | R8 | VF | VF | F |
| 22 | R1024 | S | S | S |
| 23 | NR | N | N | N |
| 24 | R32 | W | S | S |
| 25 | R16 | VF | F | W |
| 26 | R8 | W | W | W |
| 27 | R32 | W | W | S |
| 28 | R4 | N | N | VF |
| 29 | NR | N | N | N |
| 30 | R1024 | S | S | S |
| 31 | R32 | S | S | S |
| 32 | R16 | VF | W | W |
| 33 | NR | N | N | N |
| 34 | NR | N | N | N |
| 35 | R32 | W | W | S |
| 36 | R64 | F | W | W |
| 37 | R8 | VF | F | W |
| 38 | NR | N | N | N |
| 39 | R4 | N | N | VF |
| 40 | R32 | W | S | S |
| 41 | R8 | F | W | W |
| 42 | R128 | W | S | S |
| 43 | R2 | N | N | N |
| 44 | R512 | S | S | S |
| 45 | R16 | VF | W | W |
| 46 | R1024 | S | S | S |
| 47 | NR | N | N | N |
| 48 | R64 | VF | F | W |
| 49 | R512 | S | S | S |
| 50 | NR | N | N | N |
| 51 | R256 | S | S | S |
| 52 | R4 | VF | F | N |
| 53 | R128 | S | S | S |
| 54 | R32 | W | W | S |
| 55 | R2 | N | N | N |
| 56 | R256 | S | S | S |
| 57 | NR | N | N | N |
| 58 | R64 | W | W | S |
| 59 | R8 | W | W | F |
| 60 | R128 | S | S | S |

[a] RPR titer is highest dilution of reactive syphilitic serum which gives a visible reaction in the standard rapid plasma reagin (RPR) test.

Example 14

Simultaneous Detection of Non-Treponemal and Treponemal Antibodies in Human Serum or Plasma This Example demonstrates a flow-through test device that allows the simultaneous detection in a biological sample (such as, human serum or plasma) of antibodies specific for treponemal or non-treponemal (lipoidal) antigens. Such device is useful, for instance, in the diagnosis of syphilis in a subject.

The flow-through test device used in this Example included a membrane spotted with recombinant treponemal antigen, VDRL antigen (immobilized as described in the foregoing Examples) and a control. The prototype device was provided by Span Diagnostics Ltd. (173-B, New Industrial Estate, Udhna, Surat-394 210, India). The recombinant treponemal antigen, immobilized VDRL antigen, and control were arranged in a triangular configuration along the edges of the membrane (see, e.g., FIG. 10). The studies were performed with the test device resting on a horizontal surface to ensure equal distribution of the reagents during the test.

One hundred (100) µl of wash buffer was added to the center of the test device and allowed to soak in for at least 30 seconds. The wash buffer was void of organic solvents and detergents. One hundred (100) µl of a human serum or plasma was then added to the center of the test device membrane and allowed to react with the surface for at least 30 seconds. If the samples were to be kept for a short period of time, the samples were stored at 2-8° C. For longer storage, the specimens were stored at −20° C. or lower. Prior to assaying previously frozen samples, the samples were completely thawed, gently mixed and subjected to centrifugation at 2,000×g for 10 minutes. The resulting clear supernatant was then tested. The test device was subsequently washed with wash buffer (150 µl for at least 30 seconds, which allowed for solution absorption). To determine if antibodies specific for treponemal and/or non-treponemal (lipoidal) antigen(s) were present in the sample, 200 µl of SIGNAL REAGENT (Colloidal Gold Protein A Reagent) was added and allowed to soak in. For the earliest interpretation, results were read after about 2 minutes. For a final interpretation the results were read after about 10 minutes.

If a colored spot appeared only in the control area, then the sample was considered to be non-reactive for antibodies specific for either treponemal or non-treponemal (lipoidal) antigens. Reactivity in the control area alone indicated that the device was functioning properly, and further indicated a negative diagnosis for syphilis (or *T. pallidum* infection) for the subject from which the sample was obtained. If the control spot and either or both of the treponemal and/or non-treponemal antigen spots were reactive (i.e., turned color), a positive diagnosis of syphilis (or *T. pallidum* infection) in the subject was further considered (as discussed below in more detail). If, upon completion of the test, none of the control, treponemal antigen or non-treponemal antigen spots appeared reactive, then the test was considered invalid.

Table 3 illustrates the results obtaining from processing 150 samples obtained from healthy donors that had not previously been infected with *T. pallidum*.

TABLE 3

| | | | Flow-Through Test | |
|---|---|---|---|---|
| Sample Qty | VDRL Test | TPHA Test | Treponemal Spot | Non-treponemal Spot |
| 150 | +ve: 2 −ve: 148 | −ve: 150 | −ve: 150 | +ve: 2 −ve: 148 |

The VDRL and TPHA tests are solution-based tests for detecting in subject samples antibodies specific for non-treponemal (lipoidal) antigens and treponemal antigens, respectively. As shown in Table 3, the membrane-based (flow-through) test for the detection of each type of antibody in patient samples provided the identical result as the solution-based test for the corresponding antibody. Advantageously, the dual-detection flow-through test allowed both anti-treponemal and anti-non-treponemal (anti-lipoidal) antibodies to be detected in a single assay. Only two samples (1.3%) from a healthy subject showed a positive reaction with the VDRL test and the non-treponemal (lipoidal) antigen of the flow-through device. Thus, both tests had identical and low incidence of false positive results and identical and no incidence of false negative results when testing serum from subjects not infected with *T. pallidum*.

The test device was then used to analyze serum from nine patients known to be (or have been) infected with *T. pallidum* (serum from such patients is also referred to as syphilitic serum). As demonstrated in Table 4A, the membrane-based (flow-through) assay provided identical results as the solution-based tests for each sample; that is, each sample had the same reactivity in the solution-based VDRL test as for the membrane-bound non-treponemal antigen, and in the solution-based TPHA test as for the membrane-bound treponemal antigen. As described above for the "healthy" subject serum samples, the advantage of the flow-through test was the ability to use a single assay to simultaneously test patient serum for reactivity to treponemal and non-treponemal (lipoidal) antigens.

TABLE 4A

| | | | Flow-through | | |
|---|---|---|---|---|---|
| Sample No. | VDRL Test | TPHA Test | Control | Treponemal Antigen | Non-treponemal Antigen |
| 1 | + | + | + | + | + |
| 2 | + | + | + | + | + |
| 3 | + | + | + | + | + |
| 4 | + | + | + | + | + |
| 5 | + | + | + | + | + |
| 6 | + | + | + | + | + |
| 7 | + | − | + | − | + |
| 8 | + | − | + | − | + |
| 9 | + | − | + | − | + |

To compare the sensitivity of the solution-based VDRL and TPHA assays to the flow-through test device, serum from sample 6 above was selected, serially diluted, and each dilution tested as above. As demonstrated in Table 4B, the sensitivity of the flow-through device for simultaneous detection of anti-non-treponemal (anti-lipoidal) and anti-treponemal antibodies in syphilitic serum was similar to the single detection solution assay for each type of the antibody.

TABLE 4B

| | | | Flow-through | | |
|---|---|---|---|---|---|
| Dilution | VDRL Test | TPHA Test | Control | Treponemal | Non-treponemal |
| 1:10 | + | + | + | + | + |
| 1:20 | +/− | + | + | + | − |
| 1:40 | − | + | + | + | − |
| 1:80 | − | +/− | + | + | − |
| 1:160 | − | − | + | +/− | − |
| 1:320 | − | − | + | − | − |
| 1:640 | − | − | + | − | − |

Forty-two (42) patient samples were screened for anti-treponemal and anti-non-treponemal (anti-lipoidal) antibodies using the dual-detection flow-through device and the TPHA and RPR solution-based assays. In traditional testing for syphilis, patient serum often is first screened for reactivity with a non-treponemal (lipoidal antigen) antigen, for example, using the RPR test. The RPR test typically is performed in a laboratory and may take several days to complete; meanwhile, the tested patient is released from the testing facility. If the RPR test is positive, a subsequent test to determine reactivity of patient serum with treponemal antigen(s) (such as, the TPHA test) would be recommended for a positive diagnosis of syphilis. Often is it difficult to recall a patient to perform a subsequent TPHA test, which test also typically is performed in a laboratory and may take days to complete. Testing patient samples only for reactivity to treponemal antigen(s) (e.g., using the TPHA test) also has limitations because once a patient has been infected with *T. pallidum* (i.e., has had syphilis), his/her titer for anti-treponemal antibodies typically stays high even after successful treatment. Hence, a positive test for treponemal antigen alone may not be fully informative.

The performance characteristics of the flow-through device as compared to the TPHA or RPR solution-based assays in the testing of a population of 42 patients are presented in Table 5A and 5B, respectively.

TABLE 5A

|  |  | TPHA | | |
| --- | --- | --- | --- | --- |
|  |  | + | − | Total |
| Treponemal Spot | + | 20 | 4 | 24 |
|  | − | 1 | 17 | 18 |
|  |  | 21 | 21 | 42 |

The sensitivity of the flow-through device for detecting anti-treponemal antibodies was 95% and the specificity was 81%.

TABLE 5B

|  |  | RPR | | |
| --- | --- | --- | --- | --- |
|  |  | + | − | Total |
| Non-Treponemal Spot | + | 13 | 0 | 13 |
|  | − | 1 | 28 | 29 |
|  |  | 14 | 28 | 42 |

The sensitivity of the flow-through device for detecting anti-non-treponemal (anti-lipoidal) antibodies was 93% and the specificity was 100%.

Of 42 patients screened, 13 patients were found to be both RPR- and non-treponemal spot-positive (Table 5B, top left number), and 20 were found to be both TPHA- and treponemal spot-positive (Table 5A, top left number). All 13 patients who were both RPR- and non-treponemal spot-positive were also TPHA- and treponemal spot-positive. Thus, based on the results of the flow-through device alone, these 13 patients would have been treated for syphilis immediately with no need for subsequent testing.

In the use of the flow-through test device described in this Example, one, non-limiting set of clinical management recommendations are:

| Treponemal Spot | Non-treponemal Spot | Clinical Recommendation |
| --- | --- | --- |
| − | − | No action to be taken; repeat flow-through test after about 3 months, especially in populations at high-risk for syphilis |
| − | + | No syphilis treatment; investigate alternative causes for elevated anti-lipoidal antibody titer (e.g., lupus) |
| + | + | Take blood for quantitative RPR test and obtain baseline measurement; treat patient for syphilis; and repeat quantitative RPR test in 6 months to determine efficacy of treatment |
| + | − | No syphilis treatment; repeat flow-through test after about 3 months to detect active infection |

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims.

The invention is claimed:

1. A method of making an immunoassay device for detection of anti-lipoidal antibodies comprising:
   preparing a lipoidal antigen in a non-aqueous solution;
   mixing the lipoidal antigen in a non-aqueous solution with an aqueous solution to generate lipoidal micelles;
   centrifuging the lipoidal micelles to generate a supernatant comprising small lipoidal antigen micelles having an average diameter of less than 5 microns;
   applying the small lipoidal antigen micelles to the microporous membrane having a proximal sample application area and a detection zone with a predetermined pore size, wherein the small antigen micelles enter and are retained in the pores of the detection zone, thereby forming an immunoassay device for detection of anti-lipoidal antibodies.

2. The method of claim 1, wherein the immunoassay device is a flow-through or lateral flow device and the small lipoidal antigen micelles are applied in a linear distribution to form a test line.

3. The method of claim 1, further comprising washing the microporous membrane to remove unbound small lipoidal antigen micelles from the microporous membrane.

4. The method of claim 1, wherein the lipoidal antigen comprises a USR antigen, a VDRL antigen, a synthetic VDRL antigen or cardiolipin, lecithin and cholesterol.

5. The method of claim 1, wherein the lipoidal antigen comprises from about 0.001% to about 0.1% cardiolipin; from about 0.05% to about 0.5% lecithin; and/or from about 0.2% to about 5% cholesterol.

6. The method of claim 1, wherein the lipoidal antigen comprises cardiolipin, lecithin and cholesterol.

7. The method of claim 1, wherein the non-aqueous solution to aqueous solution is present as a ratio of about 1:10, about 1:15, about 2:33, or about 1:20.

8. The method of claim 1, wherein the small lipoidal antigen micelles comprise an average diameter of less than about 3 microns, less than about 1 micron, less than about 0.9 microns, less than about 0.8 microns, less than about 0.7 microns, less than about 0.6 microns, less than about 0.5 microns, less than about 0.4 microns, less than about 0.3 microns, or less than about 0.2 microns.

9. The method of claim 1, wherein the microporous membrane comprises nitrocellulose, nylon, polyvinylidene fluoride (PVDF), polyethersulfone, polycarbonate, polyester, cellulose acetate, mixed cellulose esters, or combinations thereof; and, wherein the microporous membrane comprises a predetermined pore size with an average diameter from about 0.22 micron to about 20 microns.

10. The method of claim 1, wherein the microporous membrane comprises a predetermined pore size with an average diameter from about 0.22 micron to about 0.45 micron, from about 0.22 micron to about 0.65 micron, from about 0.22 micron to about 0.8 micron, from about 0.22 micron to about 1.2 micron, from about 0.65 micron to about 3 microns, from about 0.65 micron to about 5 microns, from about 0.65 micron to about 8 microns, from about 5 microns to about 10 microns, or from about 5 microns to about 20 microns.

11. An immunoassay device made by the method of claim 1.

12. The immunoassay device of claim 11, for determining the presence or amount of an anti-lipoidal antibody in a liquid sample, further comprising a flow path from the sample application area to the detection zone; wherein the presence or amount of the anti-lipoidal antibody in the liquid sample is detected by formation of an immunocomplex in the detection zone between the anti-lipoidal antibody in the liquid sample and the retained small lipoidal antigen micelles.

13. The immunoassay device of claim 12, wherein the device is a lateral flow device and wherein the lateral flow device further comprises a conjugate pad located in the flow path, wherein the conjugate pad comprises a mobile or mobilizable detector reagent specific for the anti-lipoidal antibody.

14. The immunoassay device of claim 13, wherein the detector reagent comprises gold-conjugated Protein A, gold-conjugated Fc-specific Protein G, or gold-conjugated anti-human antibody (Fc portion).

15. The immunoassay device of claim 13, wherein the conjugate pad further comprises a mobile or mobilizable detector reagent specific for an anti-*T. pallidum* antibody or a mobile treponemal antigen.

16. The immunoassay device of claim 15, wherein the detector reagent specific for the anti-*T. pallidum* antibody comprises gold-conjugated Protein A, gold-conjugated Fc-specific Protein G, or gold-conjugated anti-human antibody (Fc portion), or the detector reagent for the mobile treponemal antigen comprises gold-labeled anti-treponemal antigen antibody.

17. A method for detecting anti-lipoidal antibodies in a subject, comprising,
applying a biological sample from a subject to the immunoassay device of claim 11; and,
detecting formation of an immunocomplex between an anti-lipoidal antibody present in the biological sample and the immobilized small lipoidal antigen micelles in the detection zone of the immunoassay device, wherein detection of formation of the immunocomplex in the detection zone indicates the presence of the anti-lipoidal antibody in the subject.

18. The method of claim 17, wherein the presence of the anti-lipoidal antibody in the subject is used to diagnose syphilis in the subject.

19. The method of claim 17, wherein the biological sample is blood or serum.

20. The method of claim 1, wherein the non-aqueous solution comprises ethanol.

21. The method of claim 1, wherein the non-aqueous solution comprises a saline solution.

22. The method of claim 1, wherein after the mixing step, the method further comprises:
centrifuging the lipoidal micelles to generate a pellet; and
resuspending the pellet in a buffer comprising 3.72% EDTA, 40% choline chloride (v/v), phosphate buffered saline pH 6.9 ±0.1, wherein centrifuging the lipoidal micelles comprises centrifuging the resuspended pellet.

23. The method of claim 1, wherein centrifuging the lipoidal micelles generates a pellet comprising large lipoidal antigen micelles having an average diameter of greater than 5 microns, and the method further comprises reducing the large lipoidal antigen micelles to small lipoidal antigen micelles having an average diameter of less than 5 microns.

24. The method of claim 23, wherein reducing the large lipoidal antigen micelles comprises filtration, sonication, differential centrifugation or a combination thereof, of the large lipoidal antigen micelles.

25. A method of making an immunoassay device for detection of anti-lipoidal antibodies comprising:
preparing a synthetic VDRL antigen in a non-aqueous solution comprising ethanol;
mixing the synthetic VDRL antigen in a non-aqueous solution with an aqueous solution comprising saline solution to generate lipoidal micelles;
centrifuging the lipoidal micelles to generate a pellet;
resuspending the pellet in a buffer comprising 3.72% EDTA, 40% choline chloride (v/v), phosphate buffered saline pH 6.9 ±0.1, thereby generating a resuspended pellet;
centrifuging the resuspended pellet to generate a supernatant comprising small lipoidal antigen micelles having an average diameter of less than 5 microns;
applying the small lipoidal antigen micelles to the microporous membrane having a proximal sample application area and a detection zone with a pore size of 5 microns to about 10 microns, wherein the small lipoidal antigen micelles enter and are retained in the pores of the detection zone, thereby forming an immunoassay device for detection of anti-lipoidal antibodies.

26. An immunoassay device made by the method of claim 25.

* * * * *

UNITED STATES PATENT AND TRADEMARK OFFICE
CERTIFICATE OF CORRECTION

| | | |
|---|---|---|
| PATENT NO. | : 8,148,057 B2 | |
| APPLICATION NO. | : 12/433626 | |
| DATED | : April 3, 2012 | |
| INVENTOR(S) | : Arnold R. Castro | |

It is certified that error appears in the above-identified patent and that said Letters Patent is hereby corrected as shown below:

In the Claims:

Column 57, line 34, claim 14, "of claim 12" should be --of claim 13--.

Signed and Sealed this
Third Day of July, 2012

David J. Kappos
*Director of the United States Patent and Trademark Office*